United States Patent
Sordillo et al.

(10) Patent No.: US 10,739,353 B2
(45) Date of Patent: *Aug. 11, 2020

(54) SUPPRESSION OF CYTOKINE RELEASE AND CYTOKINE STORM

(71) Applicants: SignPath Pharma Inc., Quakertown, PA (US); Avanti Polar Lipids, Inc., Alabaster, AL (US)

(72) Inventors: Peter P. Sordillo, New York, NY (US); Lawrence Helson, Quakertown, PA (US); Stephen W. Burgess, Chelsea, AL (US); Walter A. Shaw, Birmingham, AL (US)

(73) Assignees: Signpath Pharma, Inc., Sandy, UT (US); Avanti Polar Lipids, Inc., Alabaster, AL (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/983,844

(22) Filed: Dec. 30, 2015

(65) Prior Publication Data

US 2016/0184330 A1   Jun. 30, 2016

Related U.S. Application Data

(60) Provisional application No. 62/098,898, filed on Dec. 31, 2014, provisional application No. 62/165,567, filed on May 22, 2015, provisional application No. 62/211,450, filed on Aug. 28, 2015.

(51) Int. Cl.
| | |
|---|---|
| G01N 33/68 | (2006.01) |
| A61K 31/12 | (2006.01) |
| A61K 9/127 | (2006.01) |
| A61K 31/683 | (2006.01) |
| A61K 9/00 | (2006.01) |
| A61K 47/12 | (2006.01) |
| A61K 47/14 | (2017.01) |

(52) U.S. Cl.
CPC ....... *G01N 33/6863* (2013.01); *A61K 9/0019* (2013.01); *A61K 9/127* (2013.01); *A61K 31/12* (2013.01); *A61K 31/683* (2013.01); *A61K 47/12* (2013.01); *A61K 47/14* (2013.01); *G01N 2333/523* (2013.01); *G01N 2333/525* (2013.01); *G01N 2333/545* (2013.01); *G01N 2333/5412* (2013.01); *G01N 2333/5421* (2013.01); *G01N 2333/5428* (2013.01); *G01N 2333/55* (2013.01); *G01N 2333/57* (2013.01); *G01N 2800/24* (2013.01); *G01N 2800/52* (2013.01); *Y02A 50/385* (2018.01); *Y02A 50/387* (2018.01); *Y02A 50/397* (2018.01)

(58) Field of Classification Search
None
See application file for complete search history.

(56) References Cited

U.S. PATENT DOCUMENTS

| | | | |
|---|---|---|---|
| 7,479,498 B2 | 1/2009 | Keller | |
| 8,309,519 B2 | 11/2012 | Li et al. | |
| 8,354,276 B2 | 1/2013 | Har-Noy | |
| 2004/0259837 A1* | 12/2004 | Yesair | A61K 9/0014 514/54 |
| 2010/0075329 A1 | 3/2010 | O'Toole et al. | |
| 2014/0302000 A1* | 10/2014 | Shlieout | A61K 9/1075 424/94.2 |
| 2015/0343063 A1* | 12/2015 | Helson | G01N 33/6872 424/9.2 |

FOREIGN PATENT DOCUMENTS

WO   WO-2013186286 A1 * 12/2013

OTHER PUBLICATIONS

Lepage et al, "Effect of an organized lipid matrix on lipid absorption and clinical outcomes in patients with cystic fibrosis," The Journal of Pediatrics, vol. 141, No. 2, pp. 178-185 (Year: 2002).*
Klöppel et al, "Fibrosis of the pancreas: the initial tissue damage and the resulting pattern," Virchows Archiv, vol. 445, No. 1, pp. 1-8 (Year: 2004).*
Pinsky et a, "Serum cytokine levels in human septic shock: relation to multiple-system organ failure and mortality," Chest, vol. 103, Issue 2, pp. 565-575 (Year: 1993).*
Henry et al, "Engineered liposomes sequester bacterial exotoxins and protect from severe invasive infections in mice," Nature Biotechnology, vol. 33, No. 1, pp. 81-88 (published Nov. 2) (Year: 2014).*
Suzuki, S., et al., "Ambivalent aspects of interleukin-6 in cerebral ischemia: Inflammatory versus neurotrophic aspects." J. Cereb. Blood Flow Metab., Nov. 19, 2009;29:464-479.
Swardfager, W., et al., "A meta-analysis of cytokines in Alzheimer's disease." Biol. Psychiatry, Jun. 8, 2010;68:930-941.
Teijaro, Jr., et al., "Mapping the innate signaling cascade essential for cytokine storm during influenza virus infection." Proc. Nall. Acad. Sciences, Mar. 11, 2014; 111:3799-3804.
Thau-Zuchman, O., et al., "The anti-inflammatory drug carprofen improves long-term outcome and induces gliogenesis after traumatic brain injury." J. Neurotrauma, Jan. 20, 2012;29:375-384.

(Continued)

*Primary Examiner* — Dennis J Parad
(74) *Attorney, Agent, or Firm* — Edwin S. Flores; Chalker Flores, LLP

(57) ABSTRACT

The present invention includes methods and compositions for ameliorating symptoms or treating one or more adverse reactions triggered by infectious diseases or disease conditions that trigger a widespread release of cytokines in a subject comprising the steps of: identifying the subject in need of amelioration of symptoms or treatment of the infectious diseases or disease conditions that trigger a widespread release of cytokines; and administering one or more pharmaceutical compositions comprising a therapeutically effective amount of a curcumin extract, curcuminoids or synthetic curcumin (S-curcumin) and derivatives thereof, or empty liposomes, dissolved or dispersed in a suitable aqueous or non-aqueous medium sufficient to reduce the level of cytokines in the host.

19 Claims, 2 Drawing Sheets

(56) References Cited

OTHER PUBLICATIONS

Tisoncik, Jr., et al., "Into the eye of the cytokine storm." Microbiol. Mol. Biol. Rev., Mar. 2012;76:16-32.
Tobinick, E., et al., "Selective TNF inhibition for chronic stroke and traumatic brain injury: an observational study involving 629 consecutive patients treated with perispinal etanercept." CNS Drugs, Oct. 26, 2012;26:1051-1070.
Tuttolomondo, A., et al., "Studies of selective TNF inhibitors in the treatment of brain injury from stroke and trauma: a review of the evidence." Drug Des., Devel. Ther., Nov. 7, 2014;8:2221-2239.
Uckun, OM., et al., "Neuroprotective effects of tetracyclines on blunt head trauma: an experimental study on rats." J. Neurosci. Rural Pract., Jan.-Mar. 2015;6:27-32.
Van Tasell, BW., et al., "Contemporary reviews in cardiovascular medicine: targeting interleukin-1 in heart disease." Circulation, 2013;128:1910-1923.
Villinger, F., et al., "Markedly elevated levels of interferon (IFN)-γ, IFN-α, interleukin (IL) -2, IL-10 and tumor necrosis factor-α associated with fatal Ebola virus infection." J. Infect. Dis. 1999; 179:S188-S191.
Voronov, E., et al., "Apte RN. IL-1 is required for tumor invasiveness and angiogenesis." Proc. Natl. Acad. Sci. USA, Mar. 4, 2003;100:2645-2650.
Wang, W., et al., "Enhanced bioavailability and efficiency of curcumin for the treatment of asthma by its formulation in solid lipid nanoparticles." Int. J. Nanomedicine, Jul. 16, 2012;7:3667-3677.
Watanabe, J., et al., "Administration of TSG-6 improves memory after traumatic brain injury in mice." Neurobiol. Dis., Nov. 2013;59:86-99.
Wauquier, N., et al., "Human fatal Zaire Ebola virus infection is associated with an aberrant innate immunity and with massive lymphocyte apoptosis." PloS Neglected Tropical Diseases http;//dx.doi 10.1371/journal.pntd.2010.0000837, Oct. 5, 2010, 10 pp.
Weber, A., et al., "Interleukin-1 (IL-1) pathway." Sci. Signal, Jan. 19, 2010;3(105):cm1, 7 pp.
Winter, CD., et al., "Raised parenchymal interleukin-6 levels correlate with improved outcome after traumatic brain Injury." Brain, Nov. 25, 2003;127: 315-320.
Woodcock, T., et al., "The role of markers of inflammation in traumatic brain injury." Front. Neurol., Mar. 4, 2013;4:1-18.
Wu, A., et al., "Brain and spinal cord interaction: a dietary curcumin derivative counteracts locomotor and cognitive deficits after brain trauma." Neurorehabil. Neural. Repair, May 2011;25:322-342.
Xiao, G., et al., "Improved outcomes from the administration of progesterone for patients with acute severe traumatic brain injury: a randomized controlled trial." Crit. Care, Apr. 30, 2008;12:R61.
Xiaoling, MU., et al., "Curcumin inhibits invasion and metastasis in the human ovarian cancer cells SKOV3 by CXCL12-CXCR4 axis." African Journal of Biotechnology, Nov. 29, 2010;9:8230-8234.
Xu, N., et al., "Inflammatory cytokines: Potential biomarkers of immunologic dysfunction in autism spectrum disorders." Mediat. Inflamm., Jan. 2, 2015;531518.
Yang, SH, et al., "Interleukin 6 mediates neuroinflammation and motor coordination deficits after mild traumatic brain injury and brief hypoxia in mice." Shock, Dec. 2013;40:471-475.
Yrjanheikki, J., et al., "Tetracyclines inhibit microglial activation and are neuroprotective in global brain ischemic" Proc. Natl. Acad. Sci., Dec. 1998;95:15769-15774.
Yu, WG., et al., "Preventive action of curcumin in experimental acute pancreatitis in mouse." Indian J. Med. Res., Nov. 2011; 134:717-724.
Yuen, KY., et al., "Human infection by avian influenza H5N1." Hong Kong Med. J. Jun. 3, 2005; 11:189-199.
Zhang, R., et al., "Anti-inflammatory and immunomodulatory mechanisms of mesenchymal stem cell transplantation in experimental traumatic brain injury." J. Neuroinflamm., 2013, 10:106.
Zhu, H.T., et al., "Curcumin attenuates acute inflammatory injury by inhibiting the TLR4/MyD88/NF-κB signaling pathway in experimental traumatic brain injury." J. Neuroinflamm., 2014;11:59.
Ziebell, JM, et al., "Involvement of pro- and anti-inflammatory cytokines and chemokines in the pathophysiology of traumatic brain injury." Neurotherapeutics, Jan. 2010;7:22-30.
Lee, HF., et al., "Anti-inflammatory and neuroprotective effects of triptolide on traumatic brain injury in rats." Respir Physiol. Neurobiol., Jun. 15, 2012;182:1-8.
Lee, SM., et al., "Minocylcline reduces cell death and improves functional recovery after traumatic spinal cord injury in the rat." J. Neurotrauma, Nov. 10, 2003;20:1017-1027.
Ley, EJ., et al., "Il6 deficiency affects function after traumatic brain injury." J. Surg. Res., Jan. 11, 2011;170:253-256.
Li, B., et al., "Simvastatin attenuates microglia, astrocyte activation and decreases IL-1β level following traumatic brain injury." Neurosurgery, Jul. 2009;65:179-186.
Lust, JA., et al., "Induction of a chronic disease state in patients with smoldering or indolent multiple myeloma by targeting interleukin-1 beta induced interleukin-6 production and the myeloma proliferative component," Mayo Clin. Proc., Feb. 2009;84:114-122.
Makhija, R., et al., "Cytokine storm in acute pancreatitis." J. Hepatobiliary Pancreat. Surg., Mar. 8, 2002;9:401-410.
Marchand, F., et al., "Effects of etanercept and minoclycline in a rat model of spinal cord injury." Eur. J. Pain, Oct. 11, 2008;13:673-681.
Marlow, GJ., et a., "Why interleukin-10 supplementation does not work in Crohn's disease patients." World J Gastroenterol., Jul. 7, 2013;19:3931-3941.
Mejia, S., et al., "Minocycline reduces traumatic brain injury-mediated caspase-1 activation, tissue damage, and neurological dysfunction." Neurosurgery, Jul. 2001;48:1393-1399.
Mirza, S., et al., "Type-2 diabetes is associated with elevated levels of TNF-alpha, IL-6 and adiponectin and low levels of leptin in a population of Mexican Americans: a cross-sectional study." Cytokine, Jan. 2012;57:136-142.
Moghadamtousi, SZ., et al., "A review on antibacterial, antiviral, and antifungal activity of curcumin." BioMed Research International http://dx.doi.org/10.1155/2014/186864, Apr. 29, 2014, 13 pp.
Mohty, M., et al., "Inflammatory cytokines and acute graft-versus-host disease after reduced-intensity conditioning allogeneic stem cell transplantation." Blood, Dec. 15, 2005;106: 4407-4411.
Morganti-Kossmann, MC., et al., "Inflammatory response in acute traumatic brain injury: a double-edged sword." Curr. Opin. Crit. Care, 2012;8:101-105.
Morganti-Kossmann, MC., et al., "Production of cytokines following brain injury: beneficial and deleterious for the damaged tissue." Mol. Psychiatry, 1997;2:133-136.
Najjar, S., et al., "Neuroinflammation and psychiatric illness." J. Neuroinflamm. 2013;10:43-66.
Naseem, M., et al., "Role of melatonin in traumatic brain injury and spinal cord injury." Scientific World J., Dec. 21, 2014;586270:13.
Sun, Y., et a., "Host cytokine storm is associated with disease severity of severe fever with thrombocytopenia syndrome." J. Infect. Dis., Aug. 17, 2012;206:1085-1094.
Niesman, IR., et al., "Traumatic brain injury enhances neuroinflammation and lesion volume in caveolin deficient mice." J. Neuroinflamm., 2014;11:39.
Nighoghossian, N., et al., "Cyclosporine in acute ischemic stroke." Neurology, Jun. 2, 2015;84(22):2216-23.
Niyati, KK., et al., "Role of cytokines and toll-like receptors in the immunopathogenesis of Guillain-Barre syndrome." Mediat. Inflamm., Sep. 22, 2014:758639.
O'Connor, CA., et al., "Effects of progesterone on neurologic and morphologic outcome following diffuse traumatic brain injury in rats." Exp. Neural., Feb. 12, 2007;205:145-153.
Oh, JY., et al., "Anti-inflammatory protein TSG-6 reduces inflammatory damage to the cornea following chemical and mechanical injury." Proc. Natl. Acad. Sci., Sep. 28, 2010;107:16875-16880.
Okamoto, H., et al., "Cytokines and chemokines in neuropsychiatric syndromes of systemic lupus erythematosus." J. Biomed. Biotechnol., May 21, 2010;268436:1-8.
Okamoto, Y., et a., "Inhibition of interleukin 17 production by curcumin in mice with collagen-induced arthritis." . Biomedical Research, May 8, 2011;22:299-304.
Opal, SM., et al., "Anti-inflammatory cytokines." Chest, Apr. 4, 2000;117:1162-1172.

(56) References Cited

OTHER PUBLICATIONS

Orlando, A., et al., "Unintentional discontinuation of statins may increase mortality after traumatic brain injury in elderly patients: A preliminary observation." J. Clin. Med. Res., Mar. 21, 2013;5:168-173.
Ou, IL., et al., "Structure-activity relationship analysis of curcumin analogues on anti-influenza virus activity." FEBS J., Aug. 23, 2013;280:5829-5840.
Ozdemir, D., et al., "Effect of melatonin on brain oxidative damage induced by traumatic brain injury in immature rats" Physiol. Res., Feb. 16, 2005;54:631-637.
Pan, DS. et al., "Inhibitory effect of progesterone on inflammatory factors after experimental traumatic brain injury." Biomed. Environ. Sci., Jul. 2, 2007;20:432-438.
Park, WY., et al., "Cytokine balance in the lungs of patients with acute respiratory distress syndrome." Amer. J. Resp. Crit. Care Med., Aug. 21, 2001;164:1896-1903.
Patel, HC., et al., "Interleukin-1 in the brain. Mechanisms of action in acute neurodegeneration." Ann. NY Acad. Sci., 2003;992:39-47.
Raflee, P., et al., "Effect of curcumin on acidic pH-induced expression of IL-6 and IL-8 in human esophageal epithelial cells (HET-1A): Role of PKC, MAPKs, and NF-κB." American Journal of Physiology-Gastrointestinal and Liver Physiology, Dec. 12, 2008;296:G388-G398.
Rasras, S., et al., "The effect of simvastatin on patients with traumatic brain injury." J. Inj. Violence Res., Nov. 1, 2012;4(3 Suppl 1)63.
Reis, EAG., et al., "Cytokine response signatures in disease progression and development of severe clinical outcomes for leptospirosis." PLoS. Negl. Trop. Dis., Sep. 19, 2013;7(9):e2457.
Roozenbeek, B., et al., "Changing patterns in the epidemiology of traumatic brain injury." Nat. Rev. Neurol., Feb. 26, 2013;9:231-236.
Sanchez-Aquilar, M., et al., "Effect of rosuvastatin on cytokines after traumatic brain injury." J. Neurosurg., Jan. 4, 2013;118:669-675.
Sanderson, K.L., et al., "Interleukin-1 receptor antagonist attenuates regional neuronal cell death and cognitive dysfunction after experimental brain injury." J. Cereb. Blood Flow Metab., Mar. 1, 1999;19:1118-1125.
Sayeed, I., et al., "Progesterone as a neuroprotective factor in traumatic and ischemic brain injury." Prog. Brain Res., 2009;175:219-237.
Semple, BD., et al., "Role of CCL2 (MCP-1) in traumatic brain injury (TBI): evidence from severe TBI patients and CCL2-/- mice." J. Cereb. Blood Flow Metab., Dec. 23, 2009;30:769-782.
Senol, N., et al., "Melatonin reduces traumatic brain injury-induced oxidative stress in the cerebral cortex and blood of rats." Neural. Regen. Res., Jun. 1, 2014;9:1112-1116.
Sharma, S., et al., "A pyrazole curcumin derivative restores membrane homeostasis disrupted after brain trauma." Exp. Neural., Nov. 2010;226:191-199.
Shiozaki, T., et al., "Cerebrospinal fluid concentrations of anti-inflammatory mediators in early-phase severe traumatic brain injury." Shock, Feb. 18, 2005;23:406-410.
Shohami, E., et al., ". Inhibition of tumor necrosis factor alpha (TNF alpha) activity in rat brain is associated with cerebroprotection after closed head injury." J. Cereb. Blood Flow Metab., Jan. 8, 1996;16:378-384.
Shojo, H., et al., "Genetic and histologic evidence implicates role of inflammation in traumatic brain injury-induced apoptosis in the cerebral cortex following moderate fluid percussion injury." Neuroscience, Oct. 2010;171:1273-1282.
Singhal, A., et al., "Association between cerebrospinal fluid interleukin-6 concentrations and outcome after severe human traumatic brain injury." J. Neurotauma, Nov. 8, 2002;19:929-939.
Skolnick, BE., et al., "A clinical trial of progesterone for severe traumatic brain injury." N. Engl. J. Med., Dec. 10, 2014;371:2467-2476.
Sordillo, P.P., et al., "Curcumin and cancer stem cells: curcumin has asymmetrical effects on cancer and normal stem cells." Anticancer Res., Oct. 24, 2014;35:599-614.
Sordillo, P.P., et al., "Curcumin suppression of cytokine release and cytokine storm. A potential therapy for patients with Ebola and other severe viral infections." In Vivo, Nov. 13, 2014;29: 1-4.
St. Clair, E.W., "The calm after the cytokine storm: Lessons from the TGN1412 trial." Apr. 2008;118:1344-1347.
Johnston, S.C., et al., "Cytokine modulation correlates with severity of monkeypox disease in humans," Journal of Clinical Virology, vol. 63, Dec. 2, 2014, pp. 42-45.
Kloesch, B., et al., "Anit-inflammatory and apoptotic effects of the polyphenol curcumin on human fibroblast-like synoviocytes," International Immunopharmacology, vol. 15, Jan. 22, 2013, pp. 400-405.
Mohamadzadeh, M., et al., "How Ebola and Marburg viruses battle the immune system," Nature Publishing Group, vol. 7, Jul. 2007, pp. 556-567.
Samini, F., et al., "Curcumin pretreatment attenuates brain lesion size and improves neurological function following traumatic brain injury in the rat," Pharacology, Biochemistry and Behavior, vol. 110, Aug. 7, 2013, pp. 238-244.
Song, Y., et al., "Curcumin Protects Mice From Coxsackievirus B3-Induced Myocarditis by Inhibiting the Phosphatidylinositol 3 kinase/Akt/Nuclear Factor-κB Pathway," Journal of Cardiovascular Pharmacology and Therapeutics, vol. 18:6, Jul. 30, 2013, pp. 560-569.
Avasarala, S., et al., "Curcumin Modulates the Inflammatory Response and Inhibits Subsequent Fibrosis in a Mouse Model of Viral-induced Acute respiratory Distress Syndrome," PLoS ONE http://dx.doi.org/10.1371/journal.pone. 2013.0057285, Feb. 20, 2013, 13 pp.
Bachis, A., et al., "Interleukin-10 prevents glutamate-mediated cerebellar granule cell death by blocking caspase-3-like activity." J Neurosci., May 1, 2001; 21:3104-3112.
Bachmeier, BE., et al., "Curcumin downregulates the inflammatory cytokines CXCL1 and -2 in breast cancer cells via NFkappaB." Carcinogenesis, Nov. 4, 2007;29:779-789.
Bachstetter, AD., et al., "Attenuation of traumatic brain injury-induced cognitive impairment in mice by targeting increased cytokine levels with a small molecule experimental therapeutic." J Neuroinflamm., 2015;12:69-77.
Basu, A., et al., "The type 1 interleukin-1 receptor is essential for the efficient activation of microglia and the induction of multiple pro-inflammatory mediators in response to brain injury." J Neurosci., Jul. 15, 2002;22:6071-6082.
Branco, LM., et al., "Emerging trends in Lassa fever. Redefining the role of immunoglobulin M and inflammation in diagnosing acute infection." Virol. J., Oct. 24, 2011;8:478.
Chen, CQ., et al., "Pure curcumin increases the expression of SOCS1 and SOCS3 in myeloproliferative neoplasms through suppressing class I histone deacetylases." Carcinogenesis, Feb. 21, 2013;34:1442-1449.
Chen, DY., et al., "Curcumin inhibits influenza virus infection and haemagglutination activity." Food Chemistry, Sep. 4, 2009;119(4):1346-1351.
Chen, G., et al., "Progesterone administration modulates TLRs/NF-kappaB signaling pathway in rat brain after cortical contusion." Ann Clin Lab Sci 2008;38:65-74.
Cheong CU., et al., "Etanercept attenuates traumatic brain injury in rats by reducing brain TNF-α contents and by stimulating newly formed neurogenesis." Mediat. Inflamm., Mar. 25, 2013;620837.
Chio, CC., et al., "Etanercept attenuates traumatic brain injury in rats by reducing early microglial expression of tumor necrosis factor-α." BMC Neurosci., Mar. 15, 2013;14:33.
Chio, CC., et al., "Therapeutic evaluation of etanercept in a model of traumatic brain injury." J. Neurochem., Aug. 17, 2010;115:921-929.
Cho, ML., et al., "Cyclosporine differentially regulates interleukin-10, interleukin-15, and tumor necrosis factor α production by rheumatoid synoviocytes." Arthritis Rheum., Jan. 2002; 46:42-51.
Clark, IA., "The advent of the cytokine storm." Immunol. Cell Biol., 2007; 85:271-273.
Crack, PJ., et al., "Anti-lysophosphatidic acid antibodies improve traumatic brain injury outcomes." J. Neuroinflamm., 2014;11:37.

(56) References Cited

OTHER PUBLICATIONS

Dardiotis, E., et al., "Traumatic brain injury and inflammation: emerging role of innate and adaptive immunity. In: Agrawal A, editor. Brain Injury—Pathogenesis, Monitoring, Recovery and Management." Croatia: In Tech, 2012.

D'Elia, RM., et al., "Targeting the 'cytokine storm' for therapeutic benefit." Clin. Vaccine Immunol., Jan. 2, 2013, 20: 319-327.

Dinarello, CA., "Interleukin-1 in the pathogenesis and treatment of inflammatory diseases." Blood, Jan. 18, 2011;117:3720-3732.

Eichacker, PQ., et al., "Risk and the efficacy of anti-inflammatory agents: Retrospective and confirmatory studies of sepsis." Am. J. Respir. Crit. Care Med., Jul. 19, 2002;166:1197-1205.

Ekici, MA., et al., "Effect of etanercept and lithium chloride on preventing secondary tissue damage in rats with experimental diffuse severe brain injury." Eur. Rev. Med. Pharmacol. Sci., 2014;18:10-27.

Emsley, HC., et al., "A randomized phase II study of interleukin-1 receptor antagonist in acute stroke patients." J Neurol. Neurosurg. Psychiatry, Feb. 9, 2005; 76:1366-1372.

Erta, M., et al. "Interleukin-6, a major cytokine in the central nervous system." Int. J. Biol. Sci., Oct. 25, 2012;8:1254-1266.

Espada-Murao, LA., et al., "Dengue and soluble mediators of the innate immune system." Trop. Med. Health, Sep. 13, 2011;39:53-62.

Fahey, AJ., et al., "Constantinescu CS: Curcumin modulation of IFN-β and IL-12 signaling and cytokine induction in human T cells." J. Cell Mol. Med., Jun. 29, 2007;11:1129-1137.

Figiel, I., "Pro-inflammatory cytokine TNF-α as a neuroprotective agent in the brain." Acta Neurobiol Exp (Wars) Nov. 26, 2008;68:526-534.

Ganjali, S., et al., "Investigation of the effects of curcumin on serum cytokines in obese individuals: A randomized controlled study." The Science World J., http://dx.doi.org/10.1155/2014/898361, Nov. 11, 2014, 7 pp.

Gao, X, et al., "Cytokine and chemokine profiles in lung tissue from fatal cases of 2009 pandemic influenza A (H1N1): Role of the host immune response in pathogenesis." Am. J. Pathol., Oct. 4, 2013;183: 1258-1268.

Gauchat, JF., et l., "Cyclosporin A prevents induction of the interleukin 2 receptor gene in cultured murine thymocytes." Proc. Natl. Acad. Sci., Apr. 16, 1986;83:6430-6434.

Genovese, M.C., et al., "Combination therapy with etanercept and anakinra in the treatment of patients with rheumatoid arthritis who have been treated unsuccessfully with methotrexate." Arthritis Rheum., May 2014;50:1412-1419.

Girgis, RR., et al., "The cytokine model of schizophrenia: Emerging therapeutic strategies." Biol. Psychiatry, Feb. 15, 2014;75:292-299.

Haque A., et al., "Confronting potential influenza A (H5N1) pandemic with better vaccines." Emerging Infectious Diseases, Oct. 10, 2007; 13:1512-1518.

Hasturk, AE., et al., "Therapeutic evaluation of interleukin 1-beta antagonist Anakinra against traumatic brain injury in rats." Ulus Travma Acil Cerrahi Derg., Jan. 2015;21:1-8.

Hatton, J., et al., "Dosing and saftey of cyclosporine in patients with severe brain injury." J. Neurosurg., Oct. 2008;109:699-707.

Hayakata, T., et al., "Changes in CSF S-100B and cytokine concentrations in early-phase severe traumatic brain injury." Shock, Apr. 21, 2004;22:102-107.

Helmy, A., et al., "The cytokine response to human traumatic brain injury: temporal profiles and evidence for cerebral parenchymal production." J. Cereb. Blood Flow Metab., Aug. 18, 2010;31:658-670.

Helmy, A., et al., "Recombinant human interleukin-1 receptor antagonist in severe traumatic brain injury: a phase II randomized control tiral." J Cereb. Blood Flow Metab., Feb. 26, 2014;34:845-851.

Henrotin, Y., et al., "Biological actions of curcumin on articular chondrocytes." Osteoarthritis Cartilage Oct. 9, 2009;18:141-149.

Hernandez-Ontiveros, DG., et al., "Microglia activation as a biomarker for traumatic brain injury." Front. Neurol. Mar. 26, 2013;4:30.

Imashuku, S., "Clinical features and treatment strategies of Epstein-Barr virus-associated hemophagochytic lymphohistiocytosis." Crit. Rev. Oncol. Hematol., Dec. 18, 2001, 44:259-272.

Jain, SK., et al., "Curcumin supplementation lowers TNF-α, IL-6, IL-8, and MCP-1 secretion in high glucose-treated cultured monocytes and blood levels of TNF-α, IL-6, MCP-1, glucose, and glycosylated hemoglobin in diabetic rats." Antioxid. Redox. Signal, Aug. 1, 2008;11: 241-249.

Jobin, C., et al., "Curcumin blocks cytokine-mediated NF-κB activation and proinflammatory gene expression by inhibiting inhibitory factor I-κB kinase activity." J. Immunol., 1999;163:3474-3483.

Kalueff, AV., et al., "Intranasal administration of human IL-6 increases the severity of chemically induced seizures in rats." Neurosci. Letters, Apr. 26, 2004;365:106-110.

Kanaris, C., et al., "G408(P) cytokine storm associated multi-organ failure with poor neurological outcome during rituximab administration in a child with relapsed acute lymphoblastic leukaemia and ebv related lymphoproliferative disease." Arch. Dis. Child, 2015;100:A168.

Kaneko, A., "Tocilizumab in rheumatoid arthritis: efficacy, safety and its place in therapy." Ther. Adv. Chronic Dis., 2013;4:15-21.

Kedzierski, L., et al., "Suppressor of cytokine signaling 4 (SOCS4) protects against severe cytokine storm and enhances viral clearance during influenza infection." Plos. Pathogens http://dx.doi.org10:1371/journal.ppat.2014/1004134, May 14, 2014, pp. 13.

Kilbaugh, TJ., et al., "Cyclosporin A preserves mitochondrial function after traumatic brain injury in the immature rat and piglet." J. Neurotrauma, May 2011;28:763-774.

Kossmann, T., et al., "Intrathecal and serum interleukin-6 and the acute-phase response in patients with severe traumatic brain injuries." Shock, Aug. 3, 1995;4(5):311-317.

Kovesdi, E., et al., "Acute minocycline treatment mitigates the symptoms of mild blast-induced traumatic brain injury." Front. Neurol., Jul. 16, 2012;3:111.

Laird, MD., et al., "Curcumin attenuates cerebral edema following traumatic brain injury in mice: a possible role for aquaporin-4." J. Neurochem., Jan. 14, 2010;113:637-648.

Larsen, CM., et al., "Interleukin-1-receptor antagonist in type 2 diabetes mellitus." N. Engl. J. Med., Apr. 12, 2007;356:1517-1526.

\* cited by examiner

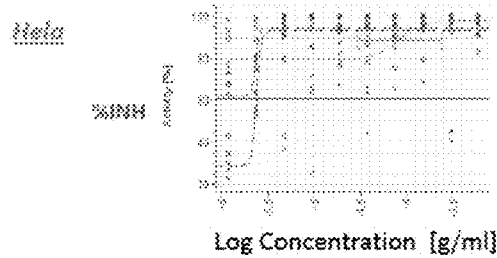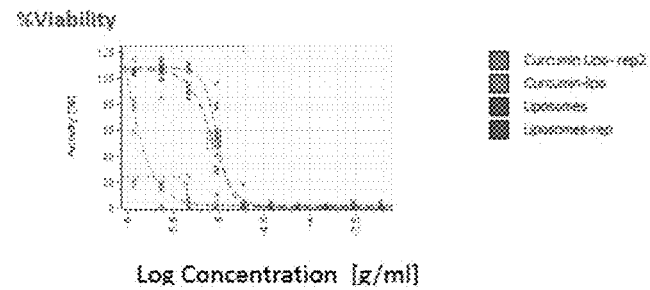
FIG. 1A  FIG. 1B
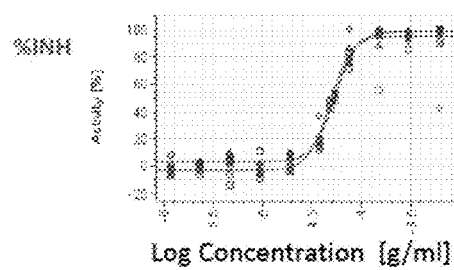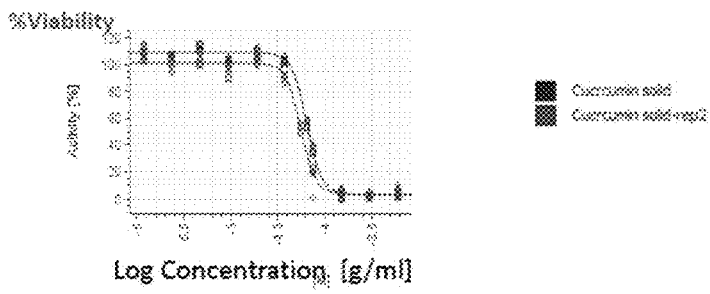
FIG. 2A  FIG. 2B
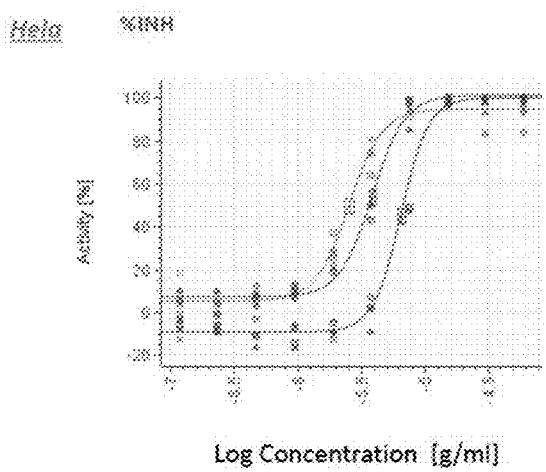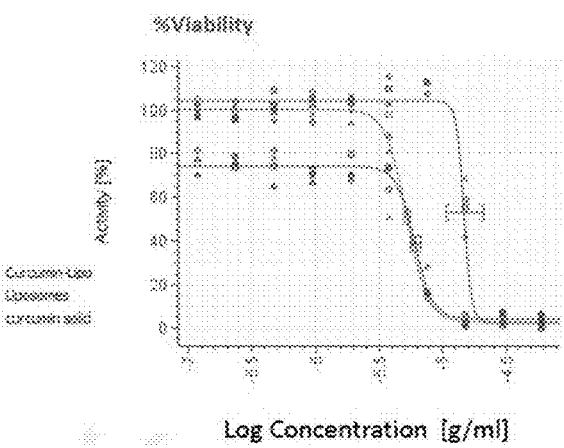
FIG. 3A  FIG. 3B

SUPPRESSION OF CYTOKINE RELEASE AND CYTOKINE STORM

CROSS-REFERENCE TO RELATED APPLICATIONS

This application claims priority to U.S. Provisional Application Ser. No. 62/098,898 filed Dec. 31, 2014, U.S. Provisional Application Ser. No. 62/165,567 filed May 22, 2015, and U.S. Provisional Application Ser. No. 62/211,450 filed Aug. 28, 2015, the entire contents of which are incorporated herein by reference.

STATEMENT OF FEDERALLY FUNDED RESEARCH

This invention was made with U.S. Government support by the USAMRIID under Project No. 1323839. The government has certain rights in this invention.

TECHNICAL FIELD OF THE INVENTION

The present invention relates in general to the field of infectious diseases and disease conditions that trigger a cytokine cascade, and more particularly, to the use of compositions that reduce the cytokine cascade.

BACKGROUND OF THE INVENTION

Without limiting the scope of the invention, its background is described in connection with infectious diseases and disease conditions that trigger, e.g., an anaphylactic cytokine cascade.

U.S. Pat. No. 8,354,276, issued to Har-Noy, entitled, "T-cell compositions that elicit type I cytokine response", relates to a method of manipulating allogeneic cells for use in allogeneic cell therapy protocols is described. The method provides a composition of highly activated allogeneic T-cells, which are infused into immunocompetent cancer patients to elicit a novel anti-tumor immune mechanism called the "Mirror Effect". The inventors argue that, in contrast to current allogeneic cell therapy protocols where T-cells in the graft mediate the beneficial graft vs. tumor (GVT) and detrimental graft vs. host (GVH) effects, the allogeneic cells of the invention stimulate host T-cells to mediate the "mirror" of these effects. The highly activated allogeneic cells of the invention are said to stimulate host immunity in a complete HLA mis-matched setting in patients that have not had a prior bone marrow transplant or received chemotherapy and/or radiation conditioning regimens.

U.S. Pat. No. 8,309,519, issued to Li, et al., is entitled "Compositions and methods for inhibiting vascular permeability" and relates to compounds, compositions and methods for inhibiting vascular permeability and pathologic angiogenesis. These inventors teach methods for producing and screening compounds and compositions capable of inhibiting vascular permeability and pathologic angiogenesis. It is said that the compositions described are useful in, methods of inhibiting vascular permeability and pathologic angiogenesis, including methods of inhibiting vascular permeability and pathologic angiogenesis induced by specific angiogenic, permeability and inflammatory factors, such as, for example VEGF, βFGF and thrombin.

U.S. Pat. No. 7,479,498, issued to Keller, is entitled "Treatments for viral infections" and relates to improved methods and compositions for treating viral infections and other diseases and conditions that induce a cytokine storm. It is further said that the invention relates to novel compositions comprising quercetin, and an anti-convulsant, such as phenytoin, in combination with multivitamins as an antiviral composition and methods of use thereof.

United States Patent Application No. 20100075329, filed by O'Toole, et al., is entitled "Methods For Predicting Production Of Activating Signals By Cross-Linked Binding Proteins" and relates to human binding proteins and antigen-binding fragments thereof that specifically bind to the human interleukin-21 receptor (IL21R), and uses therefore. The invention is said to include methods to predict whether the binding proteins of the invention may take on agonistic activities in vivo and produce a cytokine storm. In addition, the invention is said to provide methods for determining whether an anti-IL21R binding protein is a neutralizing anti-IL21R binding protein, based on the identification of several IL21-responsive genes. Finally, it is said that the binding proteins can act as antagonists of IL21R activity, thereby modulating immune responses in general, and those mediated by IL21R in particular.

SUMMARY OF THE INVENTION

In one embodiment, the present invention includes a method of ameliorating symptoms or treating one or more adverse reactions triggered by infectious diseases or disease conditions that trigger a widespread release of cytokines in a subject comprising the steps of: identifying the subject in need of amelioration of symptoms or treatment of the infectious diseases or disease conditions that trigger a widespread release of cytokines; and administering one or more pharmaceutical compositions comprising a therapeutically effective amount of a liposome or a lysophosphatidyl-monoglyceride-fatty acid eutectic, dissolved or dispersed in a suitable aqueous or non-aqueous medium sufficient to reduce the level of cytokines in the subject. In one aspect, the one or more infectious diseases are selected from at least one of viral, bacterial, fungal, helminthic, protozoan, or hemorrhagic infectious agents. In another aspect, the one or more infectious diseases is selected from at least one of infection with an Arenaviridae, Filoviridae, Bunyaviridae, Flaviviridae, and Rhabdoviridae virus. In another aspect, the one or more infectious diseases is selected from at least one of Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses. In another aspect, the one or more disease conditions is selected from at least one of cachexia, septic shock syndrome, a chronic inflammatory response, septic shock syndrome, graft versus host disease (GVHD), traumatic brain injury (e.g., cerebral cytokine storm), autoimmune diseases, multiple sclerosis, acute pancreatitis, or hepatitis. In another aspect, the one or more disease conditions is an adverse reaction caused by the treatment with anti-CD19 Chimeric Antigen Receptor (CAR) T cells or antitumor cell therapy, activated dendritic cells, activated macrophages, or activated B cells. In another aspect, the composition further comprises curcumin extract, curcuminoids or synthetic curcumin are disposed in the liposome and comprise a lipid or a phospholipid wall. In another aspect, the lipid or the phospholipid is selected from the group consisting of phosphatidylcholine (lecithin), lyso-lecithin, lysophosphatidylethanol-amine, phosphatidylserine, phosphatidylinositol, sphingomyelin, phosphatidyletha-nolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl stearate, isopropyl myristate, amphoteric acrylic polymers, fatty acid, fatty acid amides, cholesterol, cholesterol ester, diacylglycerol, and diacylglycerolsuccinate. In another aspect, the therapeutically effective amount comprises 50 nM/kg, 10 to 100 nM/kg, 25 to 75 nM/kg, 10, 20, 30, 40, 50, 60, 70, 80, 90, or 100 nM/kg of body weight of the subject. In another aspect, the synthetic curcumin is 85, 86, 87, 88, 89, 90, 91, 92, 93, 94, 95 or 96% pure diferuloylmethane. In another aspect, the composition further comprises a curcumin or curcuminoids are selected from at least one of Ar-tumerone, methylcurcumin, demethoxy curcumin, bisdemethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione (piperonyl curcumin) 1,7-bis(2-hydroxy naphthyl)-1,6-heptadiene-2,5-dione (2-hydroxyl naphthyl curcumin) and 1,1-bis(phenyl)-1,3,8,10 undecatetraene-5,7-dione. In another aspect, the composition comprises a liposome or liposome precursors comprising a lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. In another aspect, the composition comprises a eutectic mixture comprising a LysoPG, a myristoyl monoglyceride, and a myristic acid. In another aspect, the composition comprises an active agent and the composition has a ratio of phospholipids to active agent of 3:1, 1:1, 0.3:1, and 0.1:1. In another aspect, the eutectic does not interact with the active agent in vivo. In another aspect, the eutectic is provided separately from the active agent to the subject. In another aspect, the eutectic is provided in an amount that reduces QT prolongation in the subject. In another aspect, the eutectic is provided in an amount that reduces an anti-inflammatory response. In another aspect, the eutectic is provided in an amount that treats rheumatoid arthritis, psoriasis, multiple sclerosis, relapsing multiple sclerosis, or inflammatory bowel disease. In another aspect, the eutectic is provided in an amount that reduces the expression or activity of at least one of IL-1β, IL-6, TNF-α, MCP-1, MIP-1, or Rantes. In another aspect, the subject is suspected of having a traumatic brain injury and the eutectic is provided in an amount that reduces the expression or activity of at least one of TNF-α, IL-1α, IL-1β, IL-2, IL-4, IL-6, IL-8 (CXCL8), IL-10, IL-12, Interferon-γ, MCP-1 (CCL2), MIP-1α (CCL3), or TGF-β in the brain.

In another embodiment, the present invention includes a composition for ameliorating symptoms or treating one or more adverse reactions triggered by infectious diseases or disease conditions that trigger a widespread release of cytokines in a subject comprising a therapeutically effective amount of empty liposomes or a lysophosphatidyl-monoglyceride-fatty acid eutectic, dissolved or dispersed in a suitable aqueous or non-aqueous medium. In another aspect, the one or more infectious diseases are selected from at least one of viral, bacterial, fungal, helminthic, protozoan, or hemorrhagic infectious agents. In another aspect, the one or more infectious diseases is selected from at least one of infection with an Arenaviridae, Filoviridae, Bunyaviridae, Flaviviridae, and Rhabdoviridae virus. In another aspect, the one or more infectious diseases is selected from at least one of Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses. In another aspect, the one or more disease conditions is selected from at least one of cachexia, septic shock syndrome, a chronic inflammatory response, septic shock syndrome, traumatic brain injury (e.g., cerebral cytokine storm), graft versus host disease (GVHD), autoimmune diseases, multiple sclerosis, acute pancreatitis, or hepatitis. In another aspect, the one or more disease conditions is an adverse reaction caused by the treatment with anti-CD19 Chimeric Antigen Receptor (CAR) T cells or antitumor cell therapy, activated dendritic cells, activated macrophages, or activated B cells. In another aspect, the composition further comprises a curcumin extract, curcuminoids or synthetic curcumin are disposed in a liposome and comprise a lipid or a phospholipid wall. In another aspect, the liposome comprises a lipid or phospholipid, wherein lipid or the phospholipid is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl stearate, isopropyl myristate, amphoteric acrylic polymers, fatty acid, fatty acid amides, cholesterol, cholesterol ester, diacylglycerol, and diacylglycerolsuccinate. In another aspect, the composition further comprises a biodegradable polymer selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof. In another aspect, the composition adapted for intravenous, subcutaneous, intramuscular, or intraperitoneal injection in the subject. In another aspect, the composition further comprises a synthetic curcumin is 85, 86, 87, 88, 89, 90, 91, 92, 93, 94, 95 or 96% pure diferuloylmethane. In another aspect, the curcumin or curcuminoids are selected from at least one of Ar-tumerone, methylcurcumin, demethoxy curcumin, bisdemethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione (piperonyl curcumin) 1,7-bis(2-hydroxy naphthyl)-1,6-heptadiene-2,5-dione (2-hydroxyl naphthyl curcumin) and 1,1-bis(phenyl)-1,3,8,10 undecatetraene-5,7-dione. In another aspect, the composition comprises a liposome or liposome precursors comprising a lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. In another aspect, the composition comprises a eutectic mixture comprising a LysoPG, a myristoyl monoglyceride, and a myristic acid. In another aspect, the composition comprises an active agent and the composition has a ratio of phospholipids to active agent of 3:1, 1:1, 0.3:1, and 0.1:1. In another aspect, the eutectic does not interact with the active agent in vivo. In another aspect, the eutectic is provided separately from the active agent to the subject. In another aspect, the eutectic is provided in an amount that reduces QT prolongation in the subject. In another aspect, the eutectic is provided in an amount that reduces an anti-inflammatory response. In another aspect, the eutectic is provided in an amount that treats rheumatoid arthritis, psoriasis, multiple sclerosis, relapsing multiple sclerosis, or inflammatory bowel disease. In another aspect, the eutectic is provided in an amount that reduces the expression or activity of at least one of IL-1β, IL-6, TNF-α, MCP-1, MIP-1, or Rantes. In another aspect, the subject is suspected of having a traumatic brain injury and the eutectic is provided in an amount that reduces the expression or activity of at least one of TNF-α, IL-1α, IL-1β, IL-2, IL-4, IL-6, IL-8 (CXCL8), IL-10, IL-12, Interferon-γ, MCP-1 (CCL2), MIP-1α (CCL3), or TGF-β in the brain.

In another aspect, the present invention includes a method of ameliorating symptoms or treating one or more diseases or conditions that comprise a cytokine storm in a subject comprising the steps of: identifying the subject in need of amelioration of symptoms or treatment of the diseases or conditions triggered by a cytokine storm; and administering one or more pharmaceutical compositions comprising a therapeutically effective amount of an empty liposome or a lysophosphatidyl-monoglyceride-fatty acid eutectic, dissolved or dispersed in a suitable aqueous or non-aqueous medium sufficient to reduce the level of cytokines in the subject, wherein the liposome comprises a eutectic mixture comprising a LysoPG, a myristoyl monoglyceride, and a myristic acid. In another aspect, the composition comprises a liposome or liposome precursors comprising a lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. In another aspect, the composition comprises a eutectic mixture comprising a LysoPG, a myristoyl monoglyceride, and a myristic acid. In another aspect, the composition comprises an active agent and the composition has a ratio of phospholipids to active agent of 3:1, 1:1, 0.3:1, and 0.1:1. In another aspect, the eutectic does not interact with the active agent in vivo. In another aspect, the eutectic is provided separately from the active agent to the subject. In another aspect, the eutectic is provided in an amount that reduces QT prolongation in the subject. In another aspect, the eutectic is provided in an amount that reduces an anti-inflammatory response. In another aspect, the eutectic is provided in an amount that treats rheumatoid arthritis, psoriasis, multiple sclerosis, relapsing multiple sclerosis, or inflammatory bowel disease. In another aspect, the eutectic is provided in an amount that reduces the expression or activity of at least one of IL-1β, IL-6, TNF-α, MCP-1, MIP-1, or Rantes. In another aspect, the subject is suspected of having a traumatic brain injury and the eutectic is provided in an amount that reduces the expression or activity of at least one of TNF-α, IL-1α, IL-1β, IL-2, IL-4, IL-6, IL-8 (CXCL8), IL-10, IL-12, Interferon-γ, MCP-1 (CCL2), MIP-1α (CCL3), or TGF-β in the brain.

In another embodiment, the present invention includes a method of determining if a candidate drug causes an amelioration symptoms or treats one or more adverse reactions triggered by an infectious disease or a disease condition that trigger a widespread release of cytokines in a subject, the method comprising: (a) administering an amount of the candidate drug in combination with empty liposomes or a lysophosphatidyl-monoglyceride-fatty acid eutectic, and a placebo to a second subset of the patients, wherein the candidate drug is provided in an amount effective to reduce or prevent the overall level of cytokines in the subject; (b) measuring the level of cytokines in the subject from the first and second set of patients; and (c) determining if the candidate drug in combination with empty liposomes ameliorates symptoms or treats one or more adverse reactions triggered by infectious diseases or disease conditions that trigger a widespread release of cytokines is statistically significant as compared to any reduction occurring in the subset of patients that took the placebo, wherein a statistically significant reduction indicates that the candidate drug is useful in treating a disease state while also reducing or eliminating the overall level of cytokines in the subject. In another aspect, the composition comprises a liposome or liposome precursors comprising a lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. In another aspect, the composition comprises a eutectic mixture comprising a LysoPG, a myristoyl monoglyceride, and a myristic acid. In another aspect, the composition comprises an active agent and the composition has a ratio of phospholipids to active agent of 3:1, 1:1, 0.3:1, and 0.1:1. In another aspect, the eutectic does not interact with the active agent in vivo. In another aspect, the eutectic is provided separately from the active agent to the subject. In another aspect, the eutectic is provided in an amount that reduces QT prolongation in the subject. In another aspect, the eutectic is provided in an amount that reduces an anti-inflammatory response. In another aspect, the eutectic is provided in an amount that treats rheumatoid arthritis, psoriasis, multiple sclerosis, relapsing multiple sclerosis, or inflammatory bowel disease. In another aspect, the eutectic is provided in an amount that reduces the expression or activity of at least one of IL-1β, IL-6, TNF-α, MCP-1, MIP-1, or Rantes. In another aspect, the subject is suspected of having a traumatic brain injury and the eutectic is provided in an amount that reduces the expression or activity of at least one of TNF-α, IL-1α, IL-1β, IL-2, IL-4, IL-6, IL-8 (CXCL8), IL-10, IL-12, Interferon-γ, MCP-1 (CCL2), MIP-1α (CCL3), or TGF-β in the brain.

In another embodiment, the present invention includes a method of ameliorating symptoms or treating a cytokine storm caused by a therapeutic agent in a subject comprising the steps of: identifying the subject in need of amelioration of symptoms or treatment of the cytokine storm caused by a therapeutic agent; and administering one or more pharmaceutical compositions comprising a therapeutically effective amount of a curcumin extract, curcuminoids or synthetic curcumin (S-curcumin) and derivatives thereof, empty liposomes or a lysophosphatidyl-monoglyceride-fatty acid eutectic, dissolved or dispersed in a suitable aqueous or non-aqueous medium sufficient to reduce the level of cytokines in the subject. In one aspect, the therapeutic agent is selected from at least one of anti-CD19 Chimeric Antigen Receptor (CAR) T cells, an antitumor cell therapy, activated dendritic cells, activated macrophages, a tissue graft, or activated B cells. In another aspect, the composition comprises a liposome or liposome precursors comprising a lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. In another aspect, the composition comprises a eutectic mixture comprising a LysoPG, a myristoyl monoglyceride, and a myristic acid. In another aspect, the composition comprises an active agent and the composition has a ratio of phospholipids to active agent of 3:1, 1:1, 0.3:1, and 0.1:1. In another aspect, the eutectic does not interact with the active agent in vivo. In another aspect, the eutectic is provided separately from the active agent to the subject. In another aspect, the eutectic is provided in an amount that reduces QT prolongation in the subject. In another aspect, the eutectic is provided in an amount that reduces an anti-inflammatory response. In another aspect, the eutectic is provided in an amount that treats rheumatoid arthritis, psoriasis, multiple sclerosis, relapsing multiple sclerosis, or inflammatory bowel disease. In another aspect, the eutectic is provided in an amount that reduces the expression or activity of at least one of IL-1β, IL-6, TNF-α, MCP-1, MIP-1, or Rantes. In another aspect, the subject is suspected of having a traumatic brain injury and the eutectic is provided in an amount that reduces the expression or activity of at least one of TNF-α, IL-1α, IL-1β, IL-2, IL-4, IL-6, IL-8 (CXCL8), IL-10, IL-12, Interferon-γ, MCP-1 (CCL2), MIP-1α (CCL3), or TGF-β in the brain.

BRIEF DESCRIPTION OF THE DRAWINGS

For a more complete understanding of the features and advantages of the present invention, reference is now made to the detailed description of the invention along with the accompanying figures and in which:

FIGS. 1A and 1B show the percent inhibition and percent viability, respectively, achieved with liposomal curcumin in HeLa cells.

FIGS. 2A and 2B show the percent inhibition and percent viability, respectively, using solid S-curcumin curcumin in HeLa cells.

FIGS. 3A and 3B show the percent inhibition and percent viability, respectively, comparing liposomal curcumin and solid curcumin in HeLa cells.

DETAILED DESCRIPTION OF THE INVENTION

Figure 4:
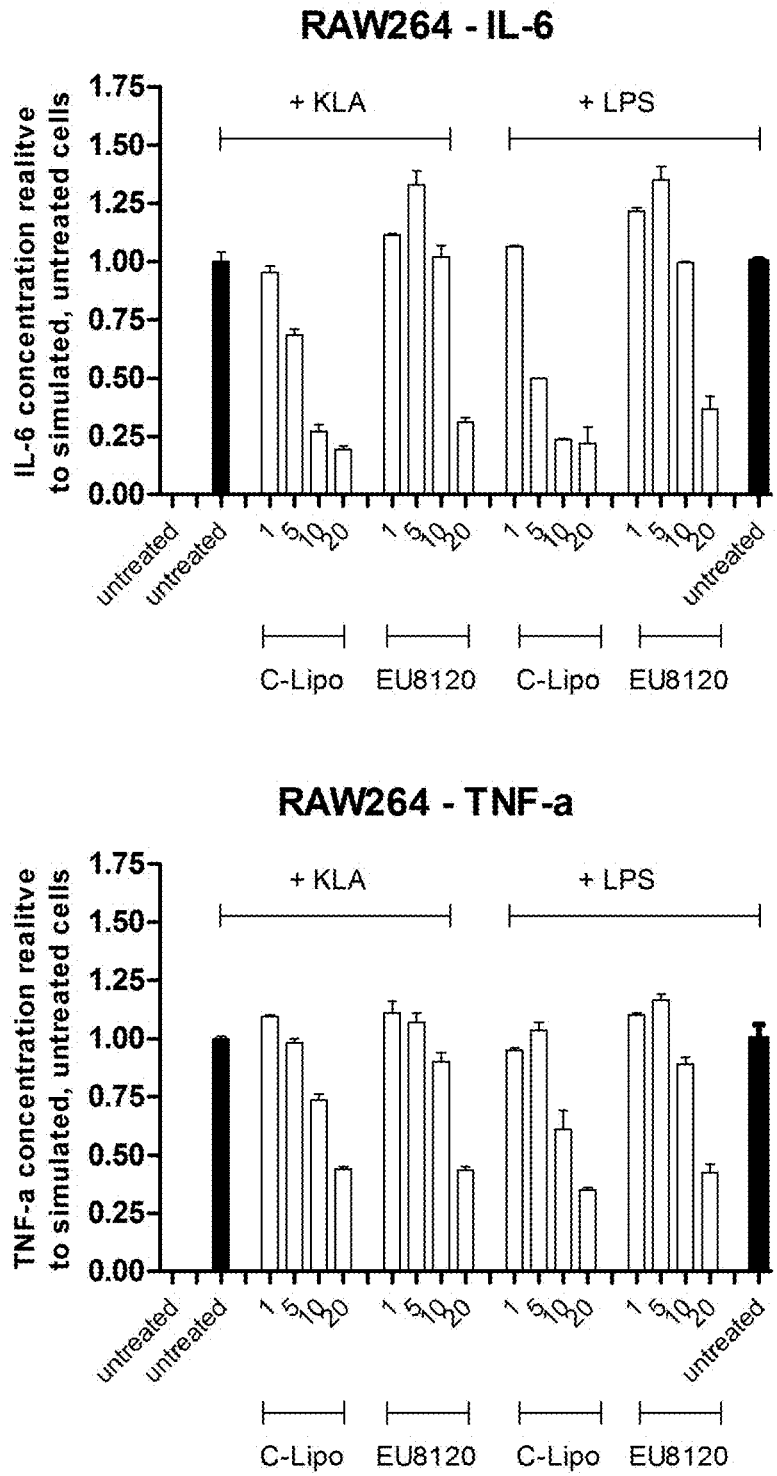
FIG. 4 shows the cytokine data (IL-6 and TNF-α) with empty liposomes compared with EU8120.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "cytokine storm" refers to the dysregulated of pro-inflammatory cytokines leading to disease has been referred to as a "cytokine storm," "cytokine release syndrome" or "inflammatory cascade". Often, a cytokine storm or cascade is referred to as being part of a sequence because one cytokine typically leads to the production of multiple other cytokines that can reinforce and amplify the immune response. Generally, these pro-inflammatory mediators have been divided into two subgroups: early mediators and late mediators. Early mediators, such as e.g., tumor-necrosis factor, interleukin-1, interleukin-6, are not sufficient therapeutic targets for re-establishing homeostatic balance because they are resolved within the time frame of a patient's travel to a clinic to receive medical attention. In contrast, the so-called "late mediators" have been targeted because it is during this later "inflammatory cascade" that the patient realizes that he or she has fallen ill.

Infectious diseases commonly associated with a "cytokine storm" include but at not limited to, malaria, avian influenza, smallpox, pandemic influenza, adult respiratory distress syndrome (ARDS), severe acute respiratory syndrome (SARS). Certain specific infectious agents include but are not limited to: infectious diseases is selected from at least one of Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabiá, Guanarito, Garissa, Ilesha, or Lassa fever viruses.

Disease conditions commonly associated with a "cytokine storm" include but at not limited to: sepsis, systemic inflammatory response syndrome (SIRS), cachexia, septic shock syndrome, traumatic brain injury (e.g., cerebral cytokine storm), graft versus host disease (GVHD), or the result of treatment with activated immune cells, e.g., IL-2 activated T cells, T cells activated with anti-CD19 Chimeric Antigen Receptor (CAR) T cells.

Generally, a cytokine storm is a healthy systemic expression of a vigorous immune system. The present invention can be used to reduce or eliminate some or most of an exaggerated immune response caused by, e.g., rapidly proliferating and highly activated T-cells or natural killer (NK) cells that results in the release of the "cytokine storm" that can include more than 150 inflammatory mediators (cytokines, oxygen free radicals, and coagulation factors). Both pro-inflammatory cytokines (such as Tumor Necrosis Factor-α, Interleukin-1, and Interkeukin-6) and anti-inflammatory cytokines (such as Interleukin-10, and Interleukin-1 receptor antagonist (IL-1RA)) become greatly elevated in, e.g., serum. It is this excessive release of inflammatory mediators that triggers the "cytokine storm."

In the absence of prompt intervention, such as that provided by the present invention, a cytokine storm can result in permanent lung damage and, in many cases, death. The end stage symptoms of the cytokine storm include but are not limited to: hypotension; tachycardia; dyspnea; fever; ischemia or insufficient tissue perfusion; uncontrollable hemorrhage; severe metabolism dysregulation; and multisystem organ failure. Deaths from infectious diseases such as Ebola virus infection are not caused by the virus itself, but rather, the cytokine storm that causes uncontrollable hemorrhaging; severe metabolism dysregulation; hypotension; tachycardia; dyspnea; fever; ischemia or insufficient tissue perfusion; and multisystem organ failure.

As used herein the term "Curcumin (diferuloyl methane; 1,7-bis(4-hydroxy-3-methoxyphenyl)-1,6-heptadiene-3,5-dione)" is a naturally occurring compound which is the main coloring principle found in the rhizomes of the plant *Curcuma longa* (U.S. Pat. No. 5,679,864 (Krackov et al.)). In one aspect, the synthetic curcumin is 85, 86, 87, 88, 89, 90, 91, 92, 93, 94, 95 or 96% pure diferuloylmethane. Non-limiting examples of curcumin and curcuminoids include, e.g., Ar-tumerone, methylcurcumin, demethoxy curcumin, bisdemethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione (piperonyl curcumin) 1,7-bis(2- hydroxy naphthyl)-1,6-heptadiene-2,5-dione (2-hydroxyl naphthyl curcumin) and 1,1-bis(phenyl)-1,3,8,10 undecatetraene-5,7-dione.

The term "liposome" refers to a capsule wherein the wall or membrane thereof is formed of lipids, especially phospholipid, with the optional addition therewith of a sterol, especially cholesterol. In one specific non-limiting example the liposomes are empty liposomes and can be formulated from a single type of phospholipid or combinations of phospholipids. The empty liposomes can further includes one or more surface modifications, such as proteins, carbohydrates, glycolipids or glycoproteins, and even nucleic acids such as aptamers, thio-modified nucleic acids, protein nucleic acid mimics, protein mimics, stealthing agents, etc. In one embodiment, the liposome is a liposome or a liposome precursor comprising a lysophosphatidyl-monoglyceride-fatty acid eutectic, such as a eutectic that includes: lysophosphatidyl compound, a monoglyceride, and free fatty acid, and in certain aspects the ratios of the composition are 1:4:2, 1:3:3, 2:4:2, or 1:2:4 mole percent lysophosphatidyl compound:monoglyceride:free fatty acid. The composition may comprise a eutectic mixture comprising a LysoPG, a myristoyl monoglyceride, and a myristic acid. In one specific, non-limiting example the composition also comprises an active agent in or about the liposome and the composition has a ratio of phospholipids to active agent of 3:1, 1:1, 0.3:1, and 0.1:1.

As used herein, the term "in vivo" refers to being inside the body. The term "in vitro" as used in the present application is to be understood as indicating an operation carried out in a non-living system.

As used herein, the term "treatment" refers to the treatment of the conditions mentioned herein, particularly in a patient who demonstrates symptoms of the disease or disorder. As used herein, the term "treating" refers to any administration of a compound of the present invention and includes (i) inhibiting the disease in an animal that is experiencing or displaying the pathology or symptomatology of the diseased (i.e., arresting further development of the pathology and/or symptomatology) or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The terms "effective amount" or "therapeutically effective amount" described herein means the amount of the subject compound that will elicit the biological or medical response of a tissue, system, animal or human that is being sought by the researcher, veterinarian, medical doctor or other clinician. In one example, the therapeutically effective amount comprises 50 nM/kg, 10 to 100 nM/kg, 25 to 75 nM/kg, 10, 20, 30, 40, 50, 60, 70, 80, 90, or 100 nM/kg of body weight of the subject.

The terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as intravenous (IV), intramuscular (IM), or intraperitoneal (IP), and the like; enteral or parenteral, transdermal dosage forms, including creams, jellies, powders, or patches; buccal dosage forms; inhalation powders, sprays, suspensions, and the like; and rectal suppositories.

As used herein the term "intravenous administration" includes injection and other modes of intravenous administration.

The term "pharmaceutically acceptable" as used herein to describe a carrier, diluent or excipient must be compatible with the other ingredients of the formulation and not deleterious to the recipient thereof.

The curcumin formulation of the present invention may comprise one or more optional pharmaceutical excipients, diluents, extended or controlled release agents, lubricants, preservatives or any combination thereof, and once solubilized may be added to injectable anti-diabetic medications or administered in a schedule depending upon the release kinetics of the curcumin formulation. A large number of biodegradable polymers may be used in the formulation of the present invention. Non-limiting examples of these polymers include polyesters, polylactides, polyglycolides, polycaprolactones polyanhydrides, polyamides, polyurethanes, polyesteramides, polydiaxanones, polyacetals, polyketals, polycarbonates, polyorthocarbonates, polyorthoesters, polyphosphoesters, polyphosphazenes, polyhydroxybuterates, polyhydroxyvalerates, polyalkelene oxalates, polyalkylene succinates, poly(malic)acid, poly(amino)acids, copolymers, terpolymers, and combinations or mixtures thereof. Specific polymers that may be used include an acrylic acid, a vinylpyrolidinome, a N-isopropylacrylamide or combinations and modifications thereof. The synthesized curcumin that is used includes curcumin, curcumin analogues, curcumin derivatives and any modifications thereof.

Treatment of Infectious Diseases. The terminal stage of Ebola and other viral diseases is often the onset of cytokine storm, the massive overproduction of cytokines by the body's immune system. The present invention includes the treatment of infectious agents that trigger a cytokine storm, such as Ebola virus, with curcumin actions to suppress cytokine release and cytokine storm.

It was found that curcumin blocks cytokine release, most importantly the key pro-inflammatory cytokines, interleukin-1, interleukin-6 and tumor necrosis factor-α. Curcumin's suppression of cytokine release correlates with clinical improvement in experimental models of disease conditions where cytokine storm plays a significant role in mortality. Thus, curcumin can be used to treat the cytokine storm of patients with Ebola. In certain examples, intravenous formulations allow achievement of therapeutic blood levels.

The high fatality rate in patients infected with the Ebola virus is thought to be due partly to the onset of cytokine storm in the advanced stages of the infection[1-2]. Cytokine storm can occur after a wide variety of infectious and non-infectious stimuli. In cytokine storm, numerous cytokines, both pro-inflammatory (IL-1, IL-6, TNF-α) and anti-inflammatory (IL-10), are released, resulting in hypotension, hemorrhage, and, ultimately, multi-organ failure. The term "cytokine storm" is most associated with the 1918 H1N1 influenza pandemic and the more recent cases of bird flu H5N1 infection[3-5]. In these cases, young people, with presumably healthy immune systems, died disproportionally from the disease, and aberrant activity of their immune systems is thought to be the cause. This syndrome has also been known to occur in advanced or terminal cases of SARS[6], Epstein-Barr virus-associated hemophagocytic lymphohistiocytosis[7], gram negative sepsis[8], malaria[9] and numerous other infectious diseases. Cytokine storm can occur from non-infectious causes, such as acute pancreatitis[10], severe burns or trauma[11] or acute respiratory distress syndrome secondary to drug use or inhalation of toxins[12]. In a recent phase 1 trial, injection of the monoclonal antibody TGN1412, which binds to the CD28 receptor on T cells, resulted in severe cases of cytokine storm and multi-organ failure in the 6 human volunteers who received this agent. This was despite the fact that the dose of this agent given was 500 times lower than had been found to be safe in animals[13].

Curcumin suppression of Cytokines.

Curcumin has been shown to inhibit the release of numerous cytokines. Abe et al showed that curcumin suppresses IL-1β, IL-8, TNF-α, monocyte chemoattractant protein-1 (MCP-1) and macrophage inflammatory protein-1α (MIP-1α) release from monocytes and macrophages[14]. Jain et al., showed that curcumin markedly reduced the release of IL-6, IL-8, TNF-α and MCP-1 from monocytes that had been cultured in a high glucose environment[15]. These same investigators studied rats with streptozotocin-induced elevated plasma blood sugar levels and significantly elevated levels of IL-6, TNF-α and MCP-1; these levels were markedly reduced by curcumin[15]. Curcumin has been reported to block the release of IL-6 in rheumatoid synovial fibroblasts[16], of IL-8 in human esophageal epithelial cells[17] and alveolar epithelial cells[18], and of IL-1 in bone marrow stromal cells[19], colonic epithelial cells[20] and human articular chondrocytes[21]. Curcumin also prevents release of IL-2[22], IL-12[22-23], Interferon-γ[22-23] and many other key cytokines[24-26] (Tables 1 and 2).

Example 1: Curcumin Cytokine Suppression Correlates with Clinical Improvement in Conditions Associated with Cytokine Storm Curcumin has positive effects on numerous disease conditions in patients and in animal systems. Avasarala et al reported on curcumin's effects on cytokine expression and disease progression in a mouse model of viral-induced acute respiratory distress syndrome. Curcumin reduced the expression of key cytokines IL-6, IL-10, interferon γ and MCP-1, and this correlated with a marked decrease in inflammation and reduction in fibrosis[27]. Yu et al showed curcumin's suppression of TNF-α levels was associated with decreased pancreatic injury in an acute pancreatitis mouse model[28]. Cheppudira et al reported that curcumin's suppression of IL-8 and GRO-α, and ultimately with NF-κB, correlated with reduction in thermal injury in a rat model[29]. Curcumin suppression of cytokines also correlates with clinical improvement in models of severe viral infection. Song et al showed that curcumin administration reduced expression of IL-1β, IL-6 and TNF-α and ultimately NF-κB, and protected against coxsackie virus-induced severe myocardial damage in infected mice[30]. Curcumin has been shown to have activity against numerous viruses, including HIV-1, HIV-2, HSV, HPV, HTLV-1, HBV, HCV, and Japanese encephalitis virus[31]. In addition, curcumin has been shown to have specific activity against the H1N1 virus in culture[32-33], although cytokine levels were not measured in these two studies. Most importantly, curcumin has been shown to stimulate the SOCS proteins[34]. These proteins have been shown to be crucial in protecting against severe cytokine storm in mice infected with influenza virus[35].

Curcumin's activity in suppressing multiple cytokines, and its activity in experimental models of diseases and conditions associated with cytokine storm, suggest it may be useful in the treatment of patients with Ebola and cytokine storm. Curcumin is poorly absorbed from the intestinal tract; however intravenous formulations may allow therapeutic curcumin blood levels to be achieved in patients diagnosed with cytokine storm. Clinical status and levels of important cytokines, such as IL-1β, IL-6 and TNF-α, should be monitored carefully when patients are treated with curcumin.

TABLE 1

Curcumin Effect on Interleukins

| Biomolecule | Key Functions |
| --- | --- |
| ↓ IL-1 | Major pro-inflammatory cytokine, hematopoesis, CNS development |
| ↓ IL-2 | T-cell lymphocyte differentiation |
| ↓ ↑ IL-4 | B-cell proliferation |
| ↓ IL-5 | Immunoglobulin secretion, eosinophil function, allergy |
| ↓ IL-6 | Major pro-inflammatory cytokine, B-cell differentiation, nerve cell differentiation |
| ↓ IL-8 | Neutrophil chemotaxis, angiogenesis |
| ↑ IL-10 | Anti-inflammatory cytokine, also has T-cell stimulatory effects |
| ↓ IL-11 | Induces acute phase proteins, antigen-antibody reactions, bone remodeling |
| ↓ IL-12 | Defense against intracellular pathogens |
| ↓ IL-13 | Induces matrix metalloproteinases, induces IgE |
| ↓ IL-17 | Pro-inflammatory cytokine |

TABLE 2

Curcumin Suppression of Other Key Cytokines

| Biomolecules | Key Functions |
| --- | --- |
| ↓ TNF-α | Major pro-inflammatory cytokine, insulin resistance, induces secretion of corticotropin releasing hormone |
| ↓ Interferon γ | Macrophage activation, T and B cell activation and differentiation |
| ↓ MCP-1 (CCL2) | Neuroinflammation, monocyte and basophil chemotaxis |
| ↓ MIP-1α (CCL3) | Activates granulocytes, induces synthesis of pro-inflammatory cytokines |
| ↓ GROα (CXCL1) | Neutrophil chemoattractant, angiogenesis, wound healing |
| ↓ GROβ (CXCL2) | Neutrophil and monocyte chemoattractant |
| ↓ IP-10 (CXCL10) | Monocyte and macrophage chemoattractant, NK cell chemoattractant, angiogenesis |
| ↓ SDF-1 (CXCL12) | Lymphocyte chemoattractant, angiogenesis, suppresses osteoclastogenesis |

Test results. First study.

Liposomes and Liposomal-Curcumin were prepared as a 6 mg/ml solutions. Curcumin (solid) was solubilized in DMSO at 6 mg/ml. All three compounds were tested in EBOV infection assay with two cell lines Hela and HFF-1. There were two sets for studies done with different dilution strategy.

Hela cell lines were used in two independent experiments (replica 1 and replica 2) and HFF-1 in one. 2 hours prior infection Liposome And Curcumin-Liposomal were diluted in media from highest concentration of 600 ug/ml (final in assay) to generate 10 points for dose response curve with 2 fold step dilution. 5 ul of each dose was dispensed by PE Janus 384-tip dispenser into assay wells with cells. The Curcumin (solid) was dispensed by HP D300 directly from the 100% DMSO stock into assay wells with cells. DMSO was normalized in all wells to final 1%. Each dose were tested 4 times on the plate n=4.

Test results. Second study.

Both cell line were used in one study (replicate 1). 2 hours prior infection Curcumin-Lip and Lip. were diluted in Media from highest concentration of 60 ug/ml (final in assay) to generate 10 points for dose response curve with 2 fold step dilution. In this case titration was done with manual mixing and changing tips for each new dose. Curcumin (solid) was tittered manually in DMSO and then equal amount for each dose was diluted 1/10 in media with mixing. 5 ul of each dose was dispensed by PE Janus 384-tip dispenser into assay wells with cells. Each dose were tested 4 times on the plate n=4. For both studies: Cells were infected with EBOV (Zaire) at MOI=0.5 for Hela cells and MOI=3 for HFF-1 and Infection was stopped in 48 h by fixing cells in formalin solution. To detect infected cells the immunostaining was done using anti-GP antibody. Images were taken by PE Opera confocal platform with 10× objective, analyzed using Acapella software.

Signal for GP-staining was converted into % infection. The number of nuclei per well was used to determine % viability of cells (in comparison to infected but untreated controls well n=16). Data was analyzed using GeneData software and % Infection converted into % Inhibition (% INH) using plate controls.

FIGS. 1A and 1B show the percent inhibition and percent viability, respectively, achieved with liposomal curcumin in HeLa cells. FIGS. 2A and 2B shows the percent inhibition and percent viability, respectively, using solid S-curcumin curcumin in HeLa cells. Similar results were obtained with the same study using HFF-1 cells.

FIGS. 3A and 3B show the percent inhibition and percent viability, respectively, comparing liposomal curcumin and solid curcumin in HeLa cells. Similar results were obtained with the same study using HFF-1 cells.

The anti-EBOV activity was determined in Hela cells and it was correlating with "cytotoxicity". Briefly, the results are as follows: (1) Curcumin-liposomal $EC_{50}$=2.5±0.2 ug/ml, safety index=2. Liposomes $EC_{50}$=3.9±0.2 ug/ml, safety index=4. Curcumin $EC_{50}$=6.5±0.5 ug/ml, safety index=1. As such, liposomes show $EC_{50}$=0.6±2 ug/ml with very good safety index ~50.

Pro-Inflammatory Cytokines in the Causation of The Prolonged QT Interval: Role of the Ceramide and Sphingosine-1 Phosphate Pathways. There is increasing evidence that excess levels of pro-inflammatory cytokines play a major role in the pathogenesis of the prolonged QT syndrome. In anti-cancer trials, QT prolongation was noted as a side effect of the cytokine, interferon γ, and QT prolongation has been seen after treatment with interleukin-18. Patients with inflammatory diseases, such as rheumatoid arthritis, psoriasis and inflammatory bowel disease, have a high incidence of QT prolongation, and die more frequently secondary to this complication. It has been shown that the degree of QT prolongation correlates directly with the extent of elevation of the key pro-inflammatory cytokines, TNF-α, IL-1β and IL-6. In large-scale studies of normal populations, it was found that asymptomatic elevations of these cytokines correlate with QT prolongation. In trials of tocilizumab, an IL-6 blocker, in patients with rheumatoid arthritis, a shortening of the duration of the previously prolonged QT interval was noted, and the degree of QT shortening correlated with the decrease in serum inflammatory markers. Studies in animal models and in cultured cardiomyocytes have shown that TNF-α suppressed IKr, IKs and Ito. This was thought to be due to the stimulation of reactive oxygen species (ROS). TNF-α and other cytokines have been shown to cause increased production of ROS. The effects of TNF-α could be blocked by administration of an anti-TNF-α antibody or by an anti-oxidant. IL-1β and IL-6 have been shown to increase the L-type Ca(2$^+$) current (ICaL), and this effect can be blocked by aspirin or indomethacin. The close link between phospholipidosis and prolonged QT provides another hint of the importance of these cytokines. 77% of the agents that can cause phospholipidosis also are hERG channel blockers. Phospholipidotic cells have been shown to secrete large amounts of TNF-α and IL-6 after LPS stimulation. It has also been speculated that the mechanism of damage from drug-induced phospholipidosis is accumulation of ceramides. Numerous studies have shown that cytokines such as interferon γ, IL-1β and TNF-α increase sphingomyelinase activation, and increase production of ceramides, which are known to suppress hERG current. It is also known that sphingolipids mediate ROS signaling. Ceramides are metabolized to sphingosine and fatty acids, and sphingosine is phosphorylated by sphingosine kinases to form sphingosine-1 phosphate. Ceramides and sphingosine-1 phosphate have opposite effects, ceramides causing apoptosis and sphingosine-1 phosphate promoting cell survival. Fingolimod, a sphingosine analogue (which has both agonist and antagonist effects on the sphingosine-1 phosphate-1 receptor), is used to treat patients with relapsing multiple sclerosis, causes QT prolongation through inhibition of the hERG current, as well as fatal ventricular arrhythmias. Further, studies in the mouse model of influenza-induced cytokine storm have shown sphingosine-1 phosphate-1 signaling to be the primary pathway for activation of the cytokine storm. The cytokine storm was reversed by a sphingosine analogue through feedback inhibition of cytokines, with marked reductions in TNF-α, IL-1α, IL-6, MCP-1, interferon α and MIP-1α, and clinical improvement seen. The survival of the mice in the study was much higher with the sphingosine analogue than with antiviral therapy. It is also noted that agents found clinically to be suppressors of QT prolongation, progestins, statins, liposomal curcumin, resveratrol, anti-oxidants, are also strong suppressors of these inflammatory cytokines. Even β-blockers, the standard treatment for patients with prolonged QT, seem to have suppression of cytokines as part of their mechanism of action in treating these patients. All these agents shift the balance away from the ceramide pathway toward the sphingosine-1 phosphate pathway. Thus, excess levels of pro-inflammatory cytokines play a major role in the causation of the prolonged QT syndrome, probably through stimulation of ROS and the ceramide pathway.

By way of explanation, and in no way a limitation of the present invention, a proposed mechanism for correction of the previously prolonged QT interval by liposomal curcumin and EU8120 is described. There is a great deal of evidence from early phase 2 anti-cancer trials of pro-inflammatory cytokines, and from recent studies on patients with rheumatoid arthritis, psoriasis and inflammatory bowel disease, suggesting increased levels of pro-inflammatory cytokines cause prolongation of the QT interval. These patients have a markedly increased incidence of prolonged QT. In addition, in trials of an anti-IL-6-antibody in patients with rheumatoid arthritis, shortening of the prolonged QT was noted, which correlated with the decrease in cytokines. The correlation of increased cytokine levels and asymptomatic QT prolongation is also found in large-scale studies of normal populations. In animal models and in ventricular myocytes, TNF-α administration causes a decrease in the rapid component of the delayed rectifier potassium current (IKr), in the slow component of the delayed rectifier current (IKs) and in the transient outward current (Ito). These effects are thought to be due to stimulation of reactive oxygen species (ROS) and can be blocked by administration of an anti-TNF-α antibody or by antioxidants. It is known from other studies that TNF-α and other pro-inflammatory cytokines stimulate ROS production. IL-1β and IL-6 also have QT prolonging effects in these models. It is also known from studies in other diseases that ROS increases ceramide production, thus shifting the balance from the sphingosine-1-phosphate (S1P) pathway (protective) to the ceramide pathway (destructive). Multiple studies in experimental models have shown that ceramides cause suppression of the hERG current. It has been proposed that statins, which reduce levels of pro-inflammatory cytokines and cause shortening of the prolonged QT, may have as their underlying mechanism the stimulation of this protective S1P pathway. Other agents that shorten the prolonged QT, including anti-oxidants, such as vitamin E, reduce levels of pro-inflammatory cytokines and of ROS, and stimulate S1P. Finally, the present inventors have recognized that the list of agents which cause both cytokine suppression and shortening of the previously prolonged QT interval is strikingly similar to the list of agents that have been shown in animal models to reduce cytokine levels and secondary brain inflammation and also reduce the degree of brain damage. Thus, the present invention can be used to target those diseases that increase ceramide production, thus shifting the balance from the sphingosine-1-phosphate (S1P) pathway (protective), to the ceramide pathway (destructive).

The present inventors have shown, in both in vitro and in vivo models, that Liposomal Curcumin and EU8120 reduce IL-1β, IL-6, TNF-α, MCP-1, MIP-1 and Rantes. Liposomes have also been shown, in other models, to compete for the enzyme sphingomyelinase and to reduce levels of ceramides, thus also shifting the ceramide/S1P balance toward S1P.

LPS-induced cytokine storm produces QTc prolongation, which is prevented by an anti-inflammatory eutectic blend. There is increasing evidence that excess levels of pro-inflammatory cytokines play a major role in the pathogenesis of the prolonged QT syndrome. Inversely, blockers such as tocilizumab (IL-6), or anti-cytokine antibodies (TNFα) contribute to a shortening of the previously-prolonged QT interval.

In this study, LPS and Kdo2-Lipid-A were used to induce cytokine release in guinea-pigs with concomitant ECG monitoring and blood draws, followed by Q-ELISA measurement of cytokine production. The guinea pig was selected because it yields reliable QTc prolongation as a result of pro-arrhythmic challenge, with consistently visible T-waves on the ECG. Male adult guinea pigs received 300 µg/kg LPS at time 0, and had ECGs analyzed at 1 h, 2 h, and 4 hours post-LPS, with simultaneous blood draw. Animals receiving LPS only exhibited a 8-msec increase in QTc after 1 h post-LPS, when TNFα levels were maximal at 5.5-fold the pre-LPS values. A 29-msec QTc prolongation 2 h post-LPS correlated with 7- and 9-fold increases in IL-1β and IL-6, respectively. The QTc prolongation remained (27 msec) after 4 hours post-LPS, when the animals were euthanized. When 9 mg/kg EU8120 (a lipid blend shown to prevent IKr-channel block by a variety of hERG blockers) was given 1 hour prior to LPS-induction, QTc prolongation was limited to 5 ms after 2 hours, and completely prevented at 1 and 4 hours post-LPS. Plasma levels of TNFα, IL1β, and IL-6 were significantly lower in EU8120-administered animals. This example demonstrates that EU8120 suppresses QTc prolongation via an anti-inflammatory cytokine-effect and not by any interaction with the active agent (LPS).

Synthetic Curcumin.

The present invention can use the compositions to treat the cytokine storm disorders using synthetic curcumin (S-curcumin).

Curcumin is the active principle of the turmeric plant, which has been synthesized to near purity (99.2%). It is formulated with liposomes, polymers, or PLGM to render it capable of being administered intravenously as a bolus or as a continuous infusion over 1-72 hours in combination with other active agents. Curcumin has antioxidant and anti-inflammatory activity, and can block autonomous intracellular signaling pathways abnormally responsive to extracellular growth factors, uncontrolled proliferation of cells and fibrosis-associated and tissue degenerative conditions. Specifically, Curcumin reacts negatively with components of key signaling pathways commanding proliferation, metabolism, survival and death.

Oral and topical administration of the extract of the turmeric plant has been used in traditional medicine for over two thousand years. While oral administration is devoid of systemic toxicity it is also devoid of systemic therapeutic activity. This is due to blood insolubility, and intestinal wall and hepatic inactivation, i.e. it has negligible bioavailability for systemic diseases by the oral route. To overcome these limitations, parenteral intravenous curcumin formulations with liposomes, polymers (n-isopropylacrylamide, N-vinylpyrrolidone and acrylic acid) and polylactic glycolic acid copolymer were entered into in pre-clinical drug development.[4]

Curcumin as an extract of turmeric root is available to researchers as a mixture of three curcuminoids and to the public as a food supplement or spice according to the FDA. The extract is 79.2% curcumin (diferuloylmethane), 18.27% demethoxycurcumin, and 2.53% bisdemethoxycurcumin.

Synthesized curcumin is GMP grade 99.2% pure diferuloylmethane produced for non-human experimental study and future Phase I clinical trials. There are obvious differences between the C3 three component extract and the single component synthesized S-curcumin that extend to discernable analytic, physicochemical, and biological characteristics. In certain aspects, the diferuloylmethane is 85, 86, 87, 88, 89, 90, 91, 92, 93, 94, 95 or 96% pure diferuloylmethane.

The present invention relates to synthetic curcumin (S-curcumin) and compares the properties and the activity of S-curcumin with liposomal curcumin, NANOCURC®, and PLGA-curcumin (hereinafter C3-complex).

Liposomal curcumin: The initial studies of liposomal curcumin were done using material bought as the complex.[6-7] Studies with S-curcumin are Mach C M, et al (2009)[8] and Mach C M et al (2010)[9].

NANOCURC®: The initial study of Nanocurc® was done using product bought as the complex Savita Bisht et al (2007)[10] used a non-sabinsa source. Since then studies with S-curcumin are used in the remainder of Nanocurc® publications.[11-13]

PLGA-curcumin: The initial studies of PLGA-curcumin were done using product manufactured as the C3-complex.[14-18] Studies included PLGA-curcumin C3 complex and PLGA-S-curcumin pharmacokinetic studies in rat brains.

Comparison of PLGA C3-complex-curcumin vs PLGA S-curcumin indicated the following differences. The solubilities of 99.2% S-Curcumin in all four solvents. Ethanol, Ethyl acetate, Acetone, and Acetonitrile, differed significantly from the C3 complex containing 76% curcumin. When normalized to equal concentrations, the pure material has greater solubility. This confers improved manufacturing capability, and attributes to different pharmacokinetics and pharmacodynamics in in vivo settings (Table 3).

TABLE 3

Solubilities of S-curcumin and C3-complex curcumin in different organic solvents.

| Solvent | Wt. of Curcumin (mg) | Vol. of solvent (µL) | Conc. (mg/mL) | Physical appearance of solubility | 1 g of solvent solubilize in solvent (mL) |
|---|---|---|---|---|---|
| Batch-C100609, Curcumin = 99.2% | | | | | |
| Ethyl acetate | 20.8 | 2000 | 10.4 | Partial | 96.2 |
| Ethanol | 17.5 | 4600 | 3.804 | Partial | 263 |
| Acetone | 46.5 | 1100 | 42.3 | Fully | 23.6 |
| Acetonitrile | 17.4 | 3200 | 5.44 | Partial | 184 |
| Batch-C3 complex, Curcumin = 76% | | | | | |
| Ethyl acetate | 21.5 | 1800 | 11.9 | Fully | 83.7 |
| Ethanol | 28.4 | 6500 | 4.37 | Fully | 229 |
| Acetone | 39.8 | 700 | 56.9 | Fully | 17.6 |
| Acetonitrile | 18.2 | 2900 | 6.28 | Fully | 159 |

*Weight the sample and transfer into a scintillation vial. Add small volume of solvent and shake well repeat for each addition till the solubility.

TABLE 4

A comparison of differences between S-Curcumin and C3-Complex curcumin.

| | C3-curcumin | S-curcumin |
|---|---|---|
| Residue on Ignition | 0.03% | 0.4% |
| Loss on drying | 0.98% | 0.24% |
| Melting range | 172-175 C. | 179.8-181.9 C. |
| Tapped bulk density | 0.61 g/ml | 0.26 g/ml |
| Loose bulk density | 0.37 g/ml | 0.18 g/ml |
| Sieve test | | |
| −40 mesh | 100% | 64.71% |
| −80 mesh | 98.27% | 64.0% |
| HPLC content curcumin | 79.2% | 99.2% |
| Total curcuminoids | 96.21% | 99.2% |
| Bisdemethoxycurcumin | 2.53% | 0 |
| Demethoxycurcumin | 18.27 | 0 |
| Heavy Metals | | |
| Lead | 0.91 ppm (ug/g) | <0.2 ppm |
| Arsenic | 0.54 ppm (ug/g) | <0.2 ppm |
| Cadmium | <0.2 ppm (ug/g) | — |
| Mercury | <0.02 ppm (ug/g) | — |
| Residual solvents | complies | complies |
| Micro-total Plate count | <100 cfu/g | 10 cfu/g |
| Yeast and mold count | <10 cfu/g | 15 cfu/g |
| *Esherichia coli* | neg/10 g | neg/10 g |
| *Salmonella* | neg/10 g | neg/10 g |
| *Staph aureus* | neg/10 g | neg/10 g |
| *Pseudomonas aeruginosa* | neg/10 g | neg/10 g |

FIG. 4 shows the cytokine data (IL-6 and TNF-α) with empty liposomes compared with the eutectic EU8120. The EU8120 used was constituted of a 1:4:2 ratio of 14:0 LysoPG/myristoyl monoglyceride/myristic fatty acid chain. EU was dissolved in water (stock 4 mM) and extensively vortexed before being added to the cells. RAW264 macrophages were pre-incubated for 24 h with empty liposomes or EU8120 before being stimulated for 24 h with KDO2 (10 ng/ml) or LPS (100 ng/ml). These data show that EU8120 like empty liposomes inhibited IL-6 and TNF-α production in KDO2 and LPS-stimulated macrophage. Empty liposomes and EU8120 were used at concentrations from 1-20 microM.

As used herein, the term "eutectic blend" refers to a mixture of chemical compounds or elements that have a chemical composition that solidifies at a lower temperature than other composition made up of the same ingredients. For example, one blended eutectic (referred to herein as EU8120) is composed of three components (14:0 Lysophosphatidylglycerol (Lyso PG), Myristoyl monoglyceride, and Myristic acid, a free fatty acid). In one non-limiting example, the blended eutectic can be made to enhance the oral bioavailability of LysoPG.

14:0 Lysophosphatidylglycerol (Lyso PG)

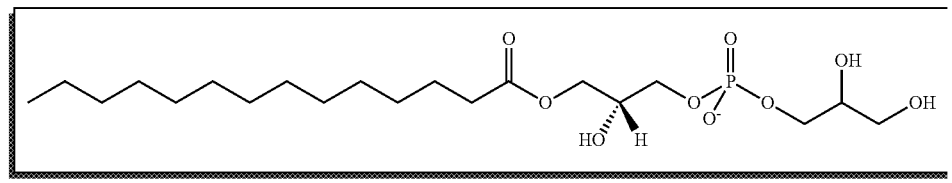

Myristoyl Monoglyceride

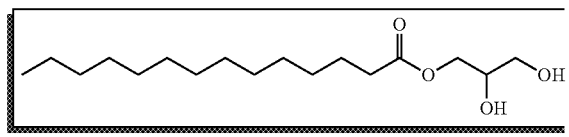

Myristic Acid, a Free Fatty Acid

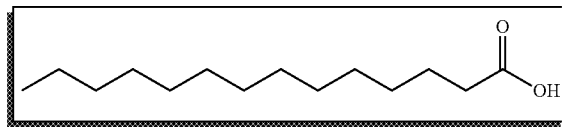

In one non-limiting example, EU8120 was constituted of a 1:4:2 ratio of 14:0 LysoPG/myristoyl monoglyceride/myristic acid chain (also referred to as myristic fatty acid). The ration can be changed to have a constituent ratio of, e.g., 2:4:2, 3:4:2, 4:4:2 (i.e., increasing the LysoPG content of EU8120).

Example 2: Additional Studies

Brain damage after traumatic brain injury (TBI) is a two-stage process: the injury caused by the initial insult is followed by a stage of inflammation where a great deal of additional damage may occur. This inflammation begins within minutes of the initial insult and can continue for months or years, and results from a complex series of metabolic processes involving marked increases in cytokines, particularly the pro-inflammatory cytokines, interleukin-1β, interleukin-6 and tumor necrosis factor-α. Levels of these cytokines may increase thousands of times more than the corresponding levels in serum. Strategies to control the levels of these pro-inflammatory cytokines and to reduce the cytokine-induced brain damage are discussed. There is extensive evidence from experiments in animal models that suppression of cytokines is effective in ameliorating neurologic damage after TBI. However, the efficacy of this approach remains to be proven in patient trials.

It is increasingly recognized that an aberrant immune system and a massive overproduction of pro-inflammatory cytokines, a 'cytokine storm', is a major factor in the disease progression and the mortality from numerous diseases. Cytokine storm, also known as 'cytokine release syndrome,' can occur after infection with malaria [1], SARS [2], dengue [3], leptospirosis [4], Lassa fever [5], gram-negative sepsis [6] as well as with numerous other infectious diseases (7-10]. Cytokine storm is a major cause of death in patients with Ebola [11-13]. Patients with cytokine storm may experience increased vascular permeability, severe hemorrhage and multi-organ failure, which may ultimately be the cause of a fatal outcome [8, 13, 14]. Marked increases in systemic cytokine levels, of both pro-inflammatory and anti-inflammatory cytokines, are seen. It is thought that this overproduction of cytokines by healthy immune systems is the explanation for why individuals from 20 to 40 were more likely to die than the elderly during the 1918 H1N1 pandemic [15, 16]. Cytokine storm can occur after severe burns or trauma [17], with acute pancreatitis [18], or with ARDS secondary to drug use or inhalation of toxins [19]. Severe acute graft vs. host disease can be considered a cytokine storm [20, 21]. Cytokine storm is also a recognized complication of treatment with the commonly-used antineoplastic agent rituximab [22], as well as of treatment with the monoclonal antibodies, tositumomab, alemtuzumab, muromonab and blinatumomab [23]. Elevated levels of cytokines are found and are thought to be an important cause of the pathology in many neurological conditions, including Alzheimer's disease [24], Parkinson's disease [25], autism [26], and multiple sclerosis [27], as well as in the acute phase of Guillian-Barre syndrome [28, 29]. Increased cytokine levels have been linked to exacerbations of psychiatric illnesses [30, 31], and of lupus encephalopathy [32, 33].

TBI represents a major health problem in the United States, with 1.7 million cases, 275 000 hospitalizations and 52 000 deaths each year [34], and neuropsychiatric sequalae are common, especially after severe injury [35]. It is now understood that cerebral damage after traumatic brain injury occurs in two stages: an initial stage where damage occurs from the external mechanical force, and a secondary inflammatory stage where damage can occur due to a cascade of processes involving cytokines such as interleukin (IL)-1β, IL-6, and tumour necrosis factor (TNF)-α [36]. The increases in cytokine levels in the brain can be massive, especially after severe TBI. IL-6 is not usually detectable in CSF, or is detectable in only very low concentrations (1-23 pg/ml) [37, 38]. In one study, CSF levels of IL-6 as high as 35 500 pg/ml were seen after severe TBI [38, 39]. These IL-6 levels were 40-100× greater than the corresponding levels in the serum of these patients [40]. Kushi et al reported very large increases in both IL-6 and IL-8, measured on admission, at 24 hours, at 72 hours and at 168 hours after severe TBI in 22 patients. In the nine fatalities, average IL-6 values at these times in the CSF were 15 241, 97 384, 548 225 and 336 500 pg/ml compared to 102, 176, 873, 3 059 pg/ml in the blood, a 'storm' of cytokines mostly localized to the brain. For the 13 survivors, average IL-6 CSF values were lower, but still much greater than in the peripheral blood: 5 376, 3 565, 328 and 764 pg/ml compared to 181, 105, 37 and 26 pg/ml in the blood [41]. Similar differences were seen for IL-8. Whereas IL-8 levels in the CSF are normally very low (5-72 pg/ml) [37], Kushi et al reported CSF IL-8 levels that were consistently elevated thousands of times more than normal levels or comparable levels in the peripheral blood [41]. These investigators also noted that IL-6 and IL-8 blood levels that remained markedly elevated after 72 hours correlated with a worse prognosis and high fatality rate. Helmy et al found marked elevations of multiple cytokines, including IL-1α, IL-1β, IL-6, IL-8, IL-10, monocyte chemotactic protein (MCP-1) and macrophage inflammatory protein-la (MIP-1α), in brain extracellular fluid after severe TBI in 12 patients. These levels were also significantly elevated compared to the corresponding blood levels [42]. Other investigators have reported similar results, and have noted that very high cytokine levels correlate with a poor prognosis [43, 44]. For example, Arand et al noted that IL-6 levels were eight-fold higher in patients who died compared to those who survived. In addition, only patients who died showed increased levels of another pro-inflammatory cytokine, IL-12 [43]. These data further support, the hypothesis that a cytokine storm is responsible for increased neurological damage after TBI. A number of studies suggest that some of these same cytokines can have beneficial as well as harmful effects on the brain [45-47]. However, it has been shown in numerous studies that blockage of these cytokines, at least in animal models, can reduce the cerebral damage after TBI. A list of key cytokines that are elevated in the brain and CSF after TBI is given in Table 5.

TABLE 5

Key cytokines show marked increases in brain and CSF after TBI

| Cytokine | Function |
| --- | --- |
| TNF-α | Major pro-inflammatory cytokine, insulin resistance, stimulates apoptosis, may also have neuroprotective functions |
| IL-1α | Pro-inflammatory cytokine, stimulates TNF-α release from endothelial cells |
| IL-1β | Major pro-inflammatory cytokine, regulates production of IL-2, IL-6, IL-8 and interferon-γ, stimulation of phagocytosis and programmed cell death, early CNS development |
| IL-2 | Pro-inflammatory cytokine, T-cell lymphocyte differentiation |
| IL-4 | Anti-inflammatory cytokine, also stimulates B-cell proliferation |
| IL-6 | Major pro-inflammatory cytokine, B-cell differentiation, neurogenesis, myokine, also has anti-inflammatory functions (suppression of IL-1 and TNF-α) |
| IL-8 (CXCL8) | Major pro-inflammatory cytokine (chemokine), neutrophil chemotaxis |
| IL-10 | Major anti-inflammatory cytokine, also has T-cell stimulatory functions |
| IL-12 | Pro-inflammatory cytokine, T-cell differentiation |
| Interferon-γ | Pro-inflammatory cytokine, T and B cell lymphocyte and macrophage activation |
| MCP-1 (CCL2) | Pro-inflammatory cytokine, monocyte and basophil chemotaxis |
| MIP-1α (CCL3) | Pro-inflammatory cytokine, induces synthesis of pro-inflammatory cytokines, activates neutrophils |
| TGF-β | Anti-inflammatory cytokine, also has pro-inflammatory functions, may have long-term harmful effects |

Interleukin-1. The IL-1 family is a group of 11 cytokines which are intimately involved in the body's response to injury or infection [48, 49], and which also play a key role in tumour angiogenesis [50] and stimulation of cancer stem cells [51]. The most important cytokines of the IL-1 group are IL-1β, IL-1α and the IL-1 receptor antagonist, IL-1RA, but the IL-1 group also includes the pro-inflammatory cytokines IL-18, IL-33 and IL-36, as well as several less well-studied cytokines. The key cytokine IL-1β is a protein produced by activated macrophages. Among its most important functions are neutrophil activation, regulation of production of other cytokines (IL-2, IL-6, IL-8, interferon-γ), regulation of mitosis, stimulation of phagocytosis, induction of fever, angiogenesis and induction of programmed cell death [48, 49]. Increased levels of IL-1β have been found in the CSF of patients with TBI, and may be detected within minutes of acute injury [38, 52, 53]. Very high levels in the CSF of TBI patients have been associated with a worsening prognosis [54, 55].

Studies in animal models have given similar results [56-60]. Kamm et al showed that IL-1β levels appeared in the rat brain after TBI within the first hour and peaked at 8 hours, with no detectable change in IL-1β levels in the blood or liver [56]. It has also been shown, in animal models, that intraventricular administration of IL-1β significantly worsens cerebral damage [61]. Most importantly, administration of an IL-1β antagonist can prevent the damage caused by this cytokine in experimental models. Administration of IL-1RA to rodents has been shown to reduce brain damage after TBI. For example, Yang et al showed that the cerebral damage caused by middle cerebral artery occlusion in mice was reduced in those animals that were previously transfected with an adenoviral vector to induce IL-1RA overexpression [62]. Jones et al showed that a single intracerebroventricular dose of IL-1RA administered to mice at the time of TBI reduced lesion volume, resulted in functional improvement and caused a major decrease in nitric oxide synthase-2-positive cells in the lesion [63-Jones]. Sanderson et al studied the effect of systemically-administered IL-1RA to Sprague Dawley rats after TBI. No effect was seen at low doses. After high-dose administration, the investigators observed decreased neuronal loss and an increase in memory and cognitive function in the animals. No improvement was seen in motor function, however [64]. Hasturk et al showed IL-1RA reduced tissue IL-1β levels and increased levels of the antioxidant enzymes catalase, superoxide dismutase and glutathione peroxidase in rats after TBI [65]. Other groups have reported similar results [66, 67]. In addition, Basu et al reported that mice lacking the IL-1 receptor experience less brain injury after a traumatic insult [68]. The investigators found decreased basal levels of IL-1, IL-6 and COX-2, as well as fewer amoeboid microglia/macrophages, suggesting the cycle of brain inflammation was prevented at this crucial step. Further, Tehranian et al have shown that transgenic mice who overexpress human IL-IRA in astrocytes have decreased levels of IL-1β, IL-6 and TNF-α compared to wild type mice, and have better neurological recovery after head injury [69].

These data suggest that the use of IL-1RA might be an effective strategy in patients with TBI. Human recombinant IL-1RA has been a standard medication for patients with rheumatoid arthritis for several years, and its use has been investigated in a number of diseases where increased cytokines play a role in the destructive process, including diabetes [70], heart failure [71], multiple myeloma [72] and sepsis [73]. In a randomized phase II trial of patients with acute stroke, there was less loss of cognitive function in patients treated with IL-1RA compared to the control group [74]. Helmy et al conducted a phase II controlled trial of this agent in 20 patients with severe TBI, and were able to conclude that IL-1RA does cross the blood-brain barrier and is safe in this population [75]. They were unable to conclude that IL-1RA administration resulted in therapeutic benefit in these patients [75]. While many of these results seem promising, however, the efficacy of IL-1RA may be limited, as it directly blocks only one of the important cytokines involved in the inflammation (IL-1RA may block other cytokines indirectly since IL-1 can cause increased expression of other cytokines), and this may be part of the explanation for the failure of this agent to have a greater than limited success against rheumatoid arthritis. Further, the use of IL-1RA in combination with TNF-α blockers is contraindicated, as severe side effects may result from their concomitant use [76].

Tumor necrosis factor-α. A second key pro-inflammatory cytokine is TNF-α. This cytokine plays an important role in the body's response to infections and to cancer. Since the report on TNF-α by Helson et al in 1975 [77], aberrant TNF-α function has been reported in numerous diseases, including conditions as diverse as diabetes [78], cardiovascular disease [79], inflammatory bowel disease [80] and Alzheimer's disease [81]. TNF blockers, such as infliximab, etanercept, and adalimumab, are standard therapies for patients with rheumatoid arthritis, ankylosing spondylitis and psoriasis. As noted, TNF-α is thought to have both beneficial and detrimental effects in patients with TBI [46]. However, results in experimental models suggest that these effects are mostly detrimental, especially when excessive levels of this cytokine are produced. Knoblach et al reported the correlation of TNF levels and the degree of brain injury and neurological impairment in rats after experimental TBI, with the highest levels of TNF at 1-4 hours after injury in rats with the most severe brain injury [82]. In addition, studies with the TNF-blocker, etanercept, have consistently shown reduction of brain damage in these animals after administration of this agent. Chio et al reported that etanercept, when given to rats after TBI reduced ischemia, increased glutamate levels, reduced neuronal and glial apoptosis and microglial activation, while also reducing the increased levels of TNF-α [83]. In a later report, these investigators concluded etanercept ameliorates brain injury by decreasing the early expression of TNF-α by microglia [84]. Ekici et al showed that the combination of etanercept and lithium chloride administered one hour after TBI reduced cerebral edema, tissue damage and TNF levels [85]. Cheong et al showed that etanercept administered to rats immediately after TBI resulted in increased 5-bromodeoxyuridine and doublecortin markers in the injured brain, suggesting that the increased TNF-α levels in the brain may be toxic to neural stem cells, thus interfering with neurogenesis [86]. Wang et al reported that the early use of this agent after injury promoted the survival of transplanted neural stem cells and facilitated neural regeneration [87]. Other groups have reported similar results using etanercept or other TNF blockers [88-91].

Although TNF blockers have been studied extensively in animal models, little work has been done to assess the potential efficacy of these agents in patients with TBI [92]. Tobinick et al reviewed the medical records of 617 patients with stroke and 12 with TBI who had been treated with etanercept. Marked improvement in neurological function was observed, even for patients treated more than 10 years after the initial insult. The investigators concluded that this supported the view that long-term inflammation, perhaps lasting many years, was a major cause of neurological impairment in these patients [93]. However, the small number of patients in the TBI group and the lack of a control group make the data in this report difficult to interpret, as it is not clear that TNF blockade was responsible for the observed improvement. Randomized trials are needed to prove benefit in TBI patients, and TNF blockers may have substantial toxicity. In addition, since TNF blockers target only a single cytokine, and since the use of these agents is contradicted in combination with IL-1 antagonists, the use of these blockers may not be the most effective strategy in treatment of these patients.

Interleukin-6. A third major pro-inflammatory cytokine is IL-6. As with TNF-α, elevated levels of IL-6 have been thought to have a role in the causation of numerous diseases, and like TNF-α, IL-6 is thought to have beneficial as well as harmful effects after TBI [94]. Indeed, IL-6 appears to have both a beneficial and a deleterious role in a number of neurological conditions [95]. IL-6 plays a key role in induction of nerve growth factor by astrocytes, and thus in the repair of the injured brain [39]. Ley et al reported that IL-6 knockout mice demonstrated reduced neurological function after TBI compared to normal mice, again suggesting IL-6 is necessary for neuronal recovery. The IL-6 knockout mice did, however, show significantly elevated levels of IL-1β [96]. The neuroprotective role of IL-6 was also suggested in a study of frontal lobe parenchymal IL-6 levels in patients after severe TBI. Markedly elevated IL-6 levels were found in survivors compared to those who died, while levels of IL-1β were not different [97]. However, the numbers in this study were small.

On the other hand, numerous studies have suggested that IL-6 has harmful effects after TBI. Conroy et al showed that IL-6 was toxic to rodent cerebellar granule neurons in culture [98]. In another study, intranasal administration of IL-6 to rats was found to increase the intensity of seizures, as well as to increase mortality [99]. Similar results were seen in transgenic mice with glial fibrillary acidic protein promoter driven-astrocyte IL-6 production [100]. Yang et al showed that motor coordination deficits in mice after mild TBI could be corrected by IL-6 blockade [101]. Similar results were reported in experimental spinal cord injury. Okada et al showed that an anti-IL-6 receptor mouse monoclonal antibody could increase functional spinal cord recovery in mice after injury [102]. Nakamura et al reported that an antibody to IL-6R decreased glial scar formation and increased recovery after spinal injury [103]. Crack et al reported that anti-lysophosphatidic acid antibodies markedly reduced brain damage in mice after experimental TBI. The investigators attributed this to a dramatic reduction in IL-6 induced secondary inflammation. The antibodies had no effect on levels of IL-1β or TNF-α [104]. Suzuki et al have suggested that the divergent results seen in these studies might be explained because IL-6's inflammatory effect seems to dominate in the acute phase after TBI, while its effect on neurogenesis may be important later on [105]. Little work has been done to investigate IL-6 blockers in patients with TBI. An anti-IL-6 antibody, tocilizumab, is available, and is used for treatment of patients with rheumatoid arthritis [106], but this agent has not been studied in this population.

Anti-inflammatory cytokines. Anti-inflammatory cytokines, such as IL-4, IL-10, IL-11 IL-13 and transforming growth factor (TGF)-β, can also be markedly elevated in inflammatory conditions. One of the major functions of these cytokines is to inhibit synthesis of pro-inflammatory cytokines [107]. IL-10 is the most important anti-inflammatory cytokine, and IL-10 levels are markedly elevated in the brain and CSF after TBI [54, 108]. Although IL-10 is known to also have pro-inflammatory functions [107], its main effect after TBI appears to be primarily protective against inflammatory damage. Kumar et al studied cytokine levels in 87 patients with severe TBI over a twelve-month period, and found that patients with an elevated IL-6/IL-10 ratio at six months had a poor prognosis [109]. Studies in cell culture and in animal models seem to confirm the protective effect of IL-10. Bachis et al showed IL-10 blocks caspase-3 and reduces neuronal death after exposure of rat cerebellar granule cells in culture to toxic doses of glutamate [110]. Knoblach et al showed that either intravenous or subcutaneous administration of IL-10 after experimental TBI in rats could reduce synthesis of IL-1 and enhance neurological recovery in the animals. Intracerebroventricular administration was not effective, however [111]. Chen et al showed that mice deficient in IL-10 failed to respond to the beneficial effects of hyperbaric oxygen treatment after TBI (112-X. Chen 2013). Bethea et al showed that IL-10 reduced TNF-α production and improved motor function after spinal cord injury in rats [113]. Similar neuroprotective effects of IL-10 were also seen in other studies of experimental spinal cord injury [114, 115]. This suggests another approach to the treatment of TBI in patients might be administration of an anti-inflammatory cytokine like IL-10. Trials of recombinant human IL-10 (ilodecakin) have been done in a number of diseases. However, results have so far been disappointing [116].

Targeting Multiple Cytokines.

Progestins. It is well known, from studies in animal systems, that progestins can reduce neuronal damage after TBI [117-121]. A major mechanism for the neuroprotection seen with progestins is the ability of these agents to suppress pro-inflammatory cytokines. Cutler et al showed that progesterone given to aged male rats after TBI reduced brain levels of IL-6 at 24, 48 and 72 hours. Decreased levels of NF-κB and COX-2 were also seen, and the rats demonstrated improved motor skills, decreased cerebral edema and decreased mortality (122-Cutler). He et al reported that intraperitoneal administration of progesterone could reduce IL-1β and TNF-α at 3 hours after injury. Similar results were seen after administration of another progestin, allopregnanolone [123]. Chen et al reported that progesterone given to rats following TBI decreased levels of IL-1β, IL-6 and TNF-α in the brain, as well as reducing apoptosis of brain tissue [124]. Pan et al showed intraperitoneal administration of progesterone reduced brain levels of TNF-α and NF-κB in rats after experimental TBI. Treated rats also had better results on the Neurological Severity Score Test [125]. Unfortunately, these results have not been confirmed in patient trials. Xiao et al did report positive results in a randomized trial of progesterone given within 8 hours of TBI [126]. However, large multicentre trials have not confirmed this. A large phase III trial of progesterone in patients with TBI conducted by The Neurologic Emergencies Treatment Trials Network was stopped early because of lack of efficacy [127]. A second major trial, SYNAPSE, a multinational, placebo-controlled trial of progesterone in 1195 patients with severe TBI, also showed no efficacy. Among the progesterone group, only 50.4% showed a favorable outcome on the Glasgow outcome scale, compared to 50.5% of patients who received placebo [128, 129].

Statins. These are 3-hydroxy-3-methylglutaryl coenzyme A reductase inhibitors, which are used to inhibit cholesterol production in the liver. These drugs are widely utilized clinically in patients with hypercholesterolemia. Statins are also known to have marked anti-inflammatory effects. Chen et al showed that lovastatin pre-administered to rats with experimental TBI caused marked decreases in IL-1β and TNF-α in the areas of brain injury at 6 hours and at 96 hours post-injury. Treated rats had significantly reduced FJB-positive degenerating neurons, and better functional recovery [130]. Simvastatin was shown to decrease brain levels of IL-1β and to reduce microglial and astrocyte activation in rats after TBI, with functional improvement on the NCS score. No change in IL-6 or TNF-α levels was noted, however [131]. Atorvastatin was found to lower both IL-6 and TNF-α in mice after TBI. Hippocampal degeneration and functional neurological deficits were reduced in the treated animals compared to controls [132]. There is also evidence that discontinuation of these statins in patients may lead to an increase in pro-inflammatory cytokines, including IL-6 [133-135], and that stopping these medications after TBI seems to lead to a worse prognosis [136]. Further, a retrospective study suggests pre-injury statin use is associated with better outcomes [137]. This has led to the suggestion that these agents be studied in patients with TBI. Only a few small trials have been reported. Tapia-Perez et al investigated the effect of rosuvastatin in patients with severe TBI and reported there was a reduction in amnesia time in the treated patients [138]. However, there was no difference in disability at 3 months. Further, this trial included only 8 rosuvastatin patients and 13 controls, while 21 of the 43 assessed TBI patients were deemed ineligible. In another small study, of 19 patients receiving 10 days of rosuvastatin and 17 controls, Sanchez-Aquilar et al reported that the rosuvastatin patients had a dramatic decrease in plasma levels of TNF-α compared to placebo and an improvement in disability scores. No effect was seen on IL-1β, IL-6 or IL-10 [139]. Rasras et al investigated the effects of a similar agent, simuvastatin, in a randomized trial of 66 patients with severe TBI; however, no difference was found between the treated and the control groups [140].

Tetracyclines. Tetracyclines have been shown, in animal models, to suppress inflammation and better outcomes in several neurological conditions. Bye et al showed that minocycline could reduce IL-1β and IL-6 expression and microglial and macrophage activation in mice after TBI. Neurological functioning was better at day 1 in treated mice, although there was no difference between treated mice and controls at day 4 [141]. Later studies by this same group did show, however, comparative improvement in the minocycline group by 6 weeks [142]. Shanchez Mejia et al reported that minocycline given to mice after TBI reduced IL-1β by inhibiting caspase-1 activation, resulting in improved neurological function and decreased lesion volume in the treated animals [143]. Lee et al showed that minocycline given to rats after spinal cord injury reduced TNF-α, increased IL-10, reduced neuronal cell death and improved motor function [144]. Yrjanheikki reported that either doxycycline or minocycline could reduce mRNA induction of IL-1β converting enzyme and protect against neuronal death after ischemic stroke [145]. Other investigators have also reported positive results with tetracyclines in animal models of TBI [146-148]. However, Turtzo et al could demonstrate no benefit in rats treated with minocycline after TBI [149]. Further, in another study, minocycline was found to cause increased ischemic brain injury in the neonatal mouse [150, 151].

Other anti-inflammatory agents. A number of other agents have shown anti-inflammatory activity in animal models of TBI. Melatonin was reported to decrease TNF-α and IL-1β and increase the number of surviving neurons in mice after TBI. The investigators felt this effect was secondary to dephosphorylation of the m-TOR pathway [152]. Other investigators have also reported positive results with melatonin in animal models [153-156].

Zhu et al reported that intraperitoneal administration of curcumin given to mice 15 minutes after TBI markedly decreased levels of IL-1β, IL-6 and MCP-1 and reduced the number of TLR4-positive microglia/macrophages, resulting in decreased neuronal apoptosis [157]. Other investigators have also reported neuroprotective effects of curcumin in animal models of TBI [158-161].

Cyclosporine is a potent, immunosuppressant drug. Because of its wide-ranging effects on cytokines [162-165], and activity in animal models [166], it has been studied in trials of patients with TBI. However, a randomized, placebo-controlled, trial of this agent in patients with TBI showed no activity [167]. A formulation of cyclosporine (neurostat) continues to be investigated in patients with TBI and other neurological conditions, although a recent report showed neurostat had no neuroprotective activity in acute ischemic stroke [168].

Many other agents which suppress pro-inflammatory cytokines have also been studied in animal models. Carprofen, a COX-2 inhibitor, which is currently used to treat arthritis in dogs and other animals, was found to markedly reduce IL-1β and IL-6, and to improve neurological functioning in mice after TBI [169]. Triptolide, a diterpenoid epoxide, which has anti-cancer activity in animal models, was found to suppress IL-1β, IL-6 and TNF-α, to increase IL-10 levels and to reduce neuronal apoptosis in Sprague-Dawley rats after experimental TBI [170]. TSG-6 (TNF-α stimulated gene/protein 6) is an anti-inflammatory agent which can suppress IL-1β, IL-6 and other pro-inflammatory cytokines (MIP-1α, MCP-1), and stimulate production of anti-inflammatory cytokines like IL-4 [171]. Watanabe et al showed that administration of this agent to mice after TBI decreased lesion size and improved neurological recovery [172]. Another agent, the CNS-penetrating, small molecule, MW151, which is known to suppress IL-1β and TNF-α, but not to affect anti-inflammatory cytokines like IL-10, has been tested in mice after TBI. This agent restored abnormal cytokine levels to normal, reduced glial activation and caused improvement in neurologic functioning in the treated animals [173]. None of these agents have been tested in patient trials, however.

The brain damage after TBI may be markedly worsened during a succeeding phase of brain inflammation. During this phase, massive increases occur in the levels of key cytokines, particularly IL-1β, IL-6 and TNF-α, a 'cerebral cytokine storm' where levels may increase thousands of times compared to their corresponding levels in serum. Although some of these cytokines, such as IL-6 and TNF-α, may have beneficial actions, evidence suggests excessive levels are harmful, since numerous studies in animal models have shown blockade of these cytokines can reduce brain injury. Thus, suppression of pro-inflammatory cytokines can limit the secondary damage caused by neuro-inflammation after TBI.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLE 1

1) Wauquier N, Becquart P, Padilla C, Baize S, Leroy E M. Human fatal Zaire Ebola virus infection is associated with an aberrant innate immunity and with massive lymphocyte apoptosis. PloS Neglected Tropical Diseases http://dx.doi 10.1371/journal.pntd. 2010.0000837.
2) Villinger F, Rollin P E, Brar S S, Chikkala N F, Winter J, Sundstrom J B, Zaki S R, Swanepoel R, Ansari A A, Peters C J. Markedly elevated levels of interferon (IFN)-γ, IFN-α, interleukin (IL)-2, IL-10 and tumor necrosis factor-α associated with fatal Ebola virus infection. J Infect Dis. 1999; 179:S188-S191.
3) Yuen K Y, Wong S S. Human infection by avian influenza H5N1. Hong Kong Med J 2005; 11:189-199.
4) Haque A, Hober D, Kasper L H: Confronting potential influenza A (H5N1) pandemic with better vaccines. Emerging Infectious Diseases 2007; 13:1512-1518.
5) Teijaro J R, Walsh K B, Rice S, Rosen H, Oldstone MBA. Mapping the innate signaling cascade essential for cytokine storm during influenza virus infection. Proc Nall Acad Sciences 2014; 111:3799-3804.
6) Huang K J, Siu I J, Theron M, Wu Y C, Liu C C, Lei H Y. An interferon-gamma related cytokine storm in SARS patients. Journal of Medical Virology 2005; 75:185-194.
7) Imashuku S. Clinical features and treatment strategies of Epstein-Barr virus-associated hemophagochytic lymphohistiocytosis. Crit. Rev. Oncol. Hematol 2002, 44:259-272.
8) Harrison C. Sepsis: Calming the cytokine storm. Nature Reviews Drug Discovery 2010; 9:360-361.
9) Clark I A, Alleva L M, Budd A C, Cowden W B. Understanding the role of inflammatory cytokines in malaria and related diseases. Travel Med Infect Dis 2008, 6:67-81.
10) Makhija R, Kingsnorth A N. Cytokine storm in acute pancreatitis. J. Hepatobiliary Pancreat Surg 2002; 9:401-410.
11) Aikawa N. Cytokine storm in the pathogenesis of multiple organ dysfunction syndrome associated with surgical insults. Nihon Geka Gakkei Zasshi 1996; 97:771-777.
12) Park W Y, Goodman R B, Steinberg K P, Ruzinsky J T, Rudella F, Park D R, Pugin J, Skeritt S J, Hudson L D, Martin T R. Cytokine balance in the lungs of patients with acute respiratory distress syndrome. Amer J Resp Crit Care Med 2001; 164:1896-1903.
13) St. Clair E W. The calm after the cytokine storm: Lessons from the TGN1412 trial. 2008; 118:1344-1347.
14) Abe Y., Hashimoto S., Horie T: Curcumin inhibition of inflammatory cytokine production by human peripheral blood monocytes and alveolar macrophages. Pharmacological Research 1999; 39:41-47.
15) Jain S K., Rains J., Croad J., Larson B., Jones K: Curcumin supplementation lowers TNF-α, IL-6, IL-8, and MCP-1 secretion in high glucose-treated cultured monocytes and blood levels of TNF-α, IL-6, MCP-1, glucose, and glycosylated hemoglobin in diabetic rats. Antioxid Redox Signal 2009; 11: 241-249.
16) Kloesch B., Becker T., Dietersdorfer E., Kiener H., Steiner G: Anti-inflammatory and apoptotic effects of the polyphenol curcumin on human fibroblast-like synoviocytes. Int Immunopharmacol 2013; 15:400-405.
17) Raflee P., Nelson V M., Manley S., Wellner M., Floer M., Binion D G., Shaker R: Effect of curcumin on acidic pH-induced expression of IL-6 and IL-8 in human esophageal epithelial cells (HET-1A): Role of PKC, MAPKs, and NF-κB. American Journal of Physiology-Gastrointestinal and Liver Physiology 2009; 296:G388-G398.
18) Biswas S K., McClure D., Jimenez L A., Megson I L., Rahman I: Curcumin induces glutathione biosynthesis and inhibits NF-κB activation and interleukin-8 release in alveolar epithelial cells: Mechanism of free radical scavenging activity. Antioxid Redox Signal 2005; 7:32-41.
19) Xu Y X., Pindolia K R., Janakiraman N., Chapman R A., Gautam S C: Curcumin inhibits IL-1α and TNF-α induction of AP-1 and NF-κB DNA-binding activity in bone marrow stromal cells. Hematopathol Mol Hematol 1997-1998; 11:49-62.
20) Jobin C., Bradham C A., Russo M P., Juma B., Narula A S., Brenner D A., Sartor R B: Curcumin blocks cytokine-mediated NF-κB activation and proinflammatory gene expression by inhibiting inhibitory factor I-κB kinase activity. J Immunol 1999; 163:3474-3483.
21) Henrotin Y., Clutterbuck A L., Allaway D., Lodwig E M., Harris P., et al: Biological actions of curcumin on articular chondrocytes. Osteoarthritis Cartilage 2010; 18:141-149.
22) Gao X., Kuo J., Jiang H., Deeb D., Liu Y., Divine G., Chapman R A., Dulchaysky S A., Gautam S C: Immunomodulatory activity of curcumin: Suppression of lymphocyte proliferation, development of cell-mediated cytotoxity, and cytokine production in vitro. Biochem Pharmacol 2004; 68:51-61.

23) Fahey A J., Robins R A., Constantinescu C S: Curcumin modulation of IFN-β and IL-12 signaling and cytokine induction in human T cells. J Cell Mol Med 2007; 11:1129-1137.
24) Bachmeier B E., Mohrenz I V., Mirisola V., Schleicher E., Romeo F., Hohneke C., Jochum M., Nerlich A G., Pfeffer U: Curcumin downregulates the inflammatory cytokines CXCL1 and −2 in breast cancer cells via NFkappaB. Carcinogenesis 2008; 29:779-789.
25) Xiaoling M U., Jing Z., Fang X., Liangdan T: Curcumin inhibits invasion and metastasis in the human ovarian cancer cells SKOV3 by CXCL12-CXCR4 axis. African Journal of Biotechnology 2010; 9:8230-8234.
26) Xu Y X., Pindolia K R., Janakiraman N., Noth C J., Chapman R A., Gautam S C: Curcumin, a compound with anti-inflammatory and anti-oxidant properties, down regulates chemokine expression in bone marrow stromal cells. Exp Hematol 1997; 25:413-422.
27) Avasarala S, Zhang F, Liu G, Wang R, London S D, London L. Curcumin modulates the inflammatory response and inhibits subsequent fibrosis in a mouse model of viral-induced acute respiratory distress syndrome. PLoS ONE http://dx.doi.org/10.1371/journal.pone. 2013.0057285.
28) Yu W G, Xu G, Ren G J, Xu X, Yuan H Q, Qi X L, Tian K L. Preventive action of curcumin in experimental acute pancreatitis in mouse. Indian J Med Res 2011; 134:717-724.
29) Cheppudira B, Greer A, Mares A, Fowler M, Garza T, Petz L, Loyd D, Clifford J. The anti-inflammatory and analgesic activity of curcumin in a rat model of full thickness thermal injury. The Journal of Pain 2013; 14:552.
30) Song Y, Ge W, Cai H, Zwang H. Curcumin protects mice from coxsackie virus B3-induced myocarditis by inhibiting the phosphatidylinositol 3 kinase/Akt/nuclear factor-κB pathway. J Cardiovasc Pharmacol Ther 2013; 18:560-569.
31) Moghadamtousi S Z, Kadir H A, Hassandarvish P, Tajik H, Abubakar S, Zandi K. A review on antibacterial, antiviral, and antifungal activity of curcumin BioMed Research International http://dx.doi.org/10.1155/2014/186864.
32) Chen D Y, Shien J H, Tiley L, Chiou S S, Wang S Y, Chang T J, Lee Y J, Chan K W, Hsu W L. Curcumin inhibits influenza virus infection and haemagglutination activity. Food Chemistry 2010; 119(4):1346-1351.
33) Ou J L, Mizushina Y, Wang S Y, Chuang D Y, Nadar M, Hsu W L. Structure-activity relationship analysis of curcumin analogues on anti-influenza virus activity. FEBS J. 2013; 280:5829-5840.
34) Chen C Q., Yu K., Yan Q X., Xing C Y., Chen Y., Yan Z., Shi Y F., Zhao K W., Gao S M: Pure curcumin increases the expression of SOCS1 and SOCS3 in myeloproliferative neoplasms through suppressing class I histone deacetylases. Carcinogenesis 2013; 34:1442-1449.
35) Kedzierski L, Linossi E M, Kolesnik T B, Day E B, Bird N L, Kile B T, Belz G T, Metcalf D, Nicola N A, Kedzierska K, Nicholson S E. Suppressor of cytokine signaling 4 (SOCS4) protects against severe cytokine storm and enhances viral clearance during influenza infection. Plos Pathogens http://dx.doi.org10:1371/journal.ppat.2014/1004134.
36) Ganjali S, Sahebkar A, Mandipour E, Jamialahmadi K, Torabi S, Akhlaghi S, Ferns G, Parizadeh S M R, Ghayour-Mobarhan M. Investigation of the effects of curcumin on serum cytokines in obese individuals: A randomized controlled study. The Science World J http://dx.doi.org/10.1155/2014/898361.
37) Kobayashi T, Hashimoto S, Horie T. Curcumin inhibition of *Dermatophagoides farinea*-induced interleukin-5 (IL-5) and granulocyte macrophage-colony stimulating factor (GM-CSF) production by lymphocytes from bronchial asthmatics. Biochemical Pharmacology 1997; 54:819-824.
38) Okamoto Y, Tanaka M, Fukui T, Masuzawa T. Inhibition of interleukin 17 production by curcumin in mice with collagen-induced arthritis. Biomedical Research 2011; 22:299-304.
39) Wang W, Zhu R, Xie Q, Li A, Xaio Y, Li K, Liu H, Cui D, Chen Y, Wang S. Enhanced bioavailability and efficiency of curcumin for the treatment of asthma by its formulation in solid lipid nanoparticles. Int J Nanomedicine 2012; 7:3667-3677.
40) Kondo A, Mogi M, Koshihara Y, Togani A. Signal transduction system for interleukin-6 and interleukin-11 synthesis stimulated by epinephrine in human osteoblasts and human osteogenic sarcoma cells. Biochemical Pharmacology 2001; 61:319-326.

REFERENCES EXAMPLE 2

[1] Clark I A, Alleva L M, Budd A C, Cowden W B. Understanding the role of inflammatory cytokines in malaria and related diseases. Travel Med Infect Dis 2008; 6:67-81.
[2] Huang K J, Siu I J, Theron M, Wu Y C, Liu C C, Lei H Y. An interferon-gamma related cytokine storm in SARS patients. J Med Virol 2005; 75:185-194.
[3] Espada-Murao L A, Morita K. Dengue and soluble mediators of the innate immune system. Trop Med Health 2011; 39:53-62.
[4] Reis E A G, Hagan J E, Ribeiro G S, Teixeira-Carvalho A, Martins-Filho O A, Montgomery R R et al. Cytokine response signatures in disease progression and development of severe clinical outcomes for leptospirosis. PLoS Negl Trop Dis. 2013; 7(9):e2457.
[5] Branco L M, Grove J N, Boisen M L, Shaffer J G, Goba A, Fullah M, Momoh M, Grant D S, Garry R F: Emerging trends in Lassa fever. Redefining the role of immunoglobulin M and inflammation in diagnosing acute infection. Virol J 2011; 8:478.
[6] Harrison C. Sepsis: calming the cytokine storm. Nat Rev Drug Discov 2010; 9:360-361.
[7] Clark I A. The advent of the cytokine storm. Immunol Cell Biol 2007; 85:271-273.
[8] D'Elia R V, Harrison K, Oyston P C, Lukaszewski R A, Clark G C. Targeting the 'cytokine storm' for therapeutic benefit. Clin Vaccine Immunol 2013; 20: 319-327.
[9] Sun Y, Jin C, Zhan F, Wang X, Liang M, Zhang Q, Ding S, Guan X, Huo X, Li C, Qu J, Wang Q, Zhang S, Zhang Y, Wang S, Xu A, Bi Z, Li D. Host cytokine storm is associated with disease severity of severe fever with thrombocytopenia syndrome. J Infect Dis 2012; 206: 1085-1094.
[10] Johnston S C, Johnson J C, Stonier S W, Lin K L, Kisalu N K, Hensley L E, Rimoin A W. Cytokine modulation correlates with severity of monkeypox disease in humans. J Clin Virol 2015; 63:42-45.
[11] Wauquier N, Becquart P, Padilla C, Baize S, Leroy E M. Human fatal Zaire Ebola virus infection is associated with an aberrant innate immunity and with massive lymphocyte apoptosis. PLoS Negl Trop Dis 2010; 4(10):e837.

[12] Sordillo P P, Helson L. Curcumin suppression of cytokine release and cytokine storm. A potential therapy for patients with Ebola and other severe viral infections. In Vivo. 2015; 29: 1-4.

[13] Mohamadzadeh M, Chen L, Schmaljohn A L. How Ebola and Marburg viruses battle the immune system. Nat Rev Immunol 2007; 7:556-567.

[14] Tisonick J R, Korth M J, Simmons C P, Farrar J, Martin T R, Katze M G. Into the eye of the cytokine storm. Microbiol Mol Biol Rev 2012; 76:16-32.

[15] Teijaro J R, Walsh K B, Rice S, Rosen H, Oldstone MBA. Mapping the innate signaling cascade essential for cytokine storm during influenza virus infection. Proc Natl Acad Sci 2014; 111:3799-3804.

[16] Goa R, Bhatnagar J, Blau D M, Greer P, Rollin D C, Denison A M, Deleon-Carnes M, Shieh W J, Sambhara S, Tumpey T M, Patel M, Liu L, Paddock C, Drew C, Shu Y, Katz J M, Zaki S R. Cytokine and chemokine profiles in lung tissue from fatal cases of 2009 pandemic influenza A (H1N1): Role of the host immune response in pathogenesis. Am J Pathol 2013; 183: 1258-1268.

[17] Aikawa N. Cytokine storm in the pathogenesis of multiple organ dysfunction syndrome associated with surgical insults. Nihon Geka Gakkei Zasshi 1996; 97:771-777.

[18] Makhija R, Kingsnorth A N. Cytokine storm in acute pancreatitis. J Hepatobiliary Pancreat Surg 2002; 9:401-410.

[19] Park W Y, Goodman R B, Steinberg K P, Ruzinsky J T, Rudella F, Park D R, Pugin J, Skeritt S J, Hudson L D and Martin T R. Cytokine balance in the lungs of patients with acute respiratory distress syndrome. Amer J Resp Crit Care Med 2001; 164:1896-1903.

[20] Ferrara J L, Abhyankar S, Gilliland D G. Cytokine storm of graft-versus-host disease: a critical effector role for interleukin-1. Transplant Proc 1993; 25:1216-1217.

[21] Mohty M, Blaise D, Faucher C, Vey N, Bouabdallah R, Stoppa A M, Viret F, Gravis G, Olive D, Gaugler B. Inflammatory cytokines and acute graft-versus-host disease after reduced-intensity conditioning allogeneic stem cell transplantation. Blood 2005; 106: 4407-4411.

[22] Kanaris C, Wynn R F, Konstantinidis A. G408(P) cytokine storm associated multi-organ failure with poor neurological outcome during rituximab administration in a child with relapsed acute lymphoblastic leukaemia and ebv related lymphoproliferative disease. Arch Dis Child 2015; 100:A168.

[23] Bugelski P J, Achuthanandam R, Capocasale R J, Treacy G, Bournan-Thio E. Monoclonal antibody-induced cytokine-release syndrome. Expert Rev Clin Immunol 2009; 5:499-521.

[24] Swardfager W, Lanctot K, Rothenburg L, Wong A, Cappell J, Hermann N. A meta-analysis of cytokines in Alzheimer's disease. Biol Psychiatry 2010; 68:930-941.

[25] Nagatsu T, Mogi M, Ichinose H, Togari A. Cytokines in Parkinson's disease. J Neural Transm Suppl 2000; 58:143-51.

[26] Xu N, Li X, Zhong Y. Inflammatory cytokines: Potential biomarkers of immunologic dysfunction in autism spectrum disorders. Mediat Inflamm, 2015; 531518.

[27] Navikas V, Link H. Review: Cytokines and the pathogenesis of multiple sclerosis. J Neurosci Res 1996; 45:322-333.

[28] Nyati K K, Prasad K N. Role of cytokines and toll-like receptors in the immunopathogenesis of Guillain-Barre syndrome. Mediat Inflamm, 2014:758639.

[29] Lu M O, Zhu J: The role of cytokines in Guillain-Barre syndrome. J Neurol 2011; 258: 533-548.

[30] Najjar S, Pearlman D M, Alper K, Najjar A, Devinsky O. Neuroinflammation and psychiatric illness. J Neuroinflamm 2013; 10:43-66.

[31] Girgis R R, Kumar S S, Brown A S. The cytokine model of schizophrenia: Emerging therapeutic strategies. Biol Psychiatry 2014; 75:292-299.

[32] Trysberg E, Carlsten H, Tarkowski A. Intrathecal cytokines in systemic lupus erythematosus with central nervous system involvement. Lupus 2000; 9:498-503.

[33] Okamoto H, Kobayashi A, Yamanaka H. Cytokines and chemokines in neuropsychiatric syndromes of systemic lupus erythematosus. J Biomed Biotechnol 2010; 268436: 1-8.

[34] Roozenbeck B, Maas A I R, Menon D K. Changing patterns in the epidemiology of traumatic brain injury. Nat Rev Neurol 2013; 9:231-236.

[35] Fork M, Bartels C, Ebert A D, Grubich C, Synowitz H, Wallesch C W. Neuropsychological sequelae of diffuse traumatic brain injury. Brain Inj 2005; 19:101-108.

[36] Dardiotis E, Karanikas V, Paterakis K, Fountas K, Hadjigeorgiou G M. Traumatic brain injury and inflammation: emerging role of innate and adaptive immunity. In: Agrawal A, editor. Brain Injury-Pathogenesis, Monitoring, Recovery and Management. Croatia: In Tech, 2012.

[37] Maier B, Laurer H L, Rose S, Buurman W A, Marzi I. Physiological levels of pro- and anti-inflammatory mediators in cerebrospinal fluid and plasma: a normative study. J Neurotrauma 2005; 22:822-835.

[38] Woodcock T, Morganti-Kossmann M C. The role of markers of inflammation in traumatic brain injury. Front Neurol 2013; 4:1-18.

[39] Kossmann T, Hans V, Imhof H G, Trentz O, Morganti-Kossman M C. Interleukin-6 released in human cerebrospinal fluid following traumatic brain injury may trigger nerve growth factor production in astrocytes. Brain Res 1996; 713:143-152.

[40] Kossmann T, Hans V H, Imhof H G, Stocker R, Grob P, Trentz O, Morganti-Kossman C. Intrathecal and serum interleukin-6 and the acute-phase response in patients with severe traumatic brain injuries. Shock 1995; 4(5): 311-317.

[41] Kushi H, Saito T, Makino K, Hayashi N. IL-8 is a key mediator of inflammation in severe traumatic brain injuries. Acta Neurochir Suppl 2003; 86:347-350.

[42] Helmy A, Carpenter K L H, Menon D K, Pickard J D, Hutchinson P J A. The cytokine response to human traumatic brain injury: temporal profiles and evidence for cerebral parenchymal production. J Cereb Blood Flow Metab 2011; 31:658-670.

[43] Arand M, Melzner H, Kinzl L, Bruckner U B, Gebhard F. Early inflammatory mediator response following isolated traumatic brain injury and other major trauma in humans. Langenbecks Arch Surg 2001; 386:241-248.

[44] Woiciechowsky C, Schoning B, Cobanov J, Lanksch W R, Volk H D, Docke W D. Early IL-6 plasma concentrations correlate with severity of brain injury and pneumonia in brain-injured patients. J Trauma 2002; 52:339-345.

[45] Lenzlinger P M, Morganti-Kossmann M C, Laurer H L, McIntosh T K. The duality of the inflammatory response to traumatic brain injury. Mol Neurobiol 2001; 24:169-181.

[46] Figiel I. Pro-inflammatory cytokine TNF-α as a neuroprotective agent in the brain. Acta Neurobiol Exp (Wars) 2008; 68:526-534.

[47] Morganti-Kossmann M C, Lenzlinger P M, Hans V, Stahel P, Csuka E, Ammann E, Stocker R, Trentz O, Kossmann T. Production of cytokines following brain injury: beneficial and deleterious for the damaged tissue. Mol Psychiatry 1997; 2:133-136.

[48] Dinarello C A. Interleukin-1 in the pathogenesis and treatment of inflammatory diseases. Blood 2011; 117:3720-3732.

[49] Weber A, Wasiliew P, Kracht M. Interleukin-1 (IL-1) pathway. Sci Signal 2010; 3(105):cml.

[50] Voronov E, Shouval D S, Krelin Y, Cagnano E, Benharroch D, Iwakura Y, Dinarello C A, Apte R N. IL-1 is required for tumor invasiveness and angiogenesis. Proc Natl Acad Sci USA 2003; 100:2645-2650.

[51] Sordillo P P, Helson L. Curcumin and cancer stem cells: curcumin has asymmetrical effects on cancer and normal stem cells. Anticancer Res 2015; 35:599-614.

[52] Singhal A, Baker A J, Hare G M, Reinders F X, Schlichter L C, Moulton R J. Association between cerebrospinal fluid interleukin-6 concentrations and outcome after severe human traumatic brain injury. J Neurotauma 2002; 19:929-939.

[53] Frugier T, Morganti-Kossmann M C, O'Reilly D, McLean C A. In situ detection of inflammatory mediators in post mortem human brain tissue after traumatic injury. J Neurotrauma 2010; 27:497-507.

[54] Shiozaki T, Hayakata T, Tasaki O, Hosotubo H, Fuijita K, Mouri T, et al. Cerebrospinal fluid concentrations of anti-inflammatory mediators in early-phase severe traumatic brain injury. Shock 2005; 23:406-410.

[55] Hayakata T, Shiozaki T, Tasaki O, Ikegawa H, Inoue Y, Toshiyuki F, et al. Changes in CSF S-100B and cytokine concentrations in early-phase severe traumatic brain injury. Shock 2004; 22:102-107.

[56] Kamm K, Vanderkolk W, Lawrence C, Jonker M, Davis A T. The effect of traumatic brain injury upon concentration and expression of interleukin-1beta and interleukin-10 in the rat. J Trauma 2006; 60:152-157.

[57] Shojo H, Kaunko Y, Mabuchi T, Kibayashi K, Adachi N, Borlongan C V. Genetic and histologic evidence implicates role of inflammation in traumatic brain injury-induced apoptosis in the cerebral cortex following moderate fluid percussion injury. Neuroscience 2010; 171:1273-1282.

[58] Maegele M, Saneriand S, Bouillon B, Schafer U, Trubel H, Riess P, et al. Differential immunoresponses following experimental traumatic brain injury, bone fracture and 'two-hit'-combined neurotrauma. Inflamm Res 2007; 56:318-323.

[59] Semple B D, Bye N, Rancan M, Ziebell J M, Morganti-Kossmann M C. Role of CCL2 (MCP-1) in traumatic brain injury (TBI): evidence from severe TBI patients and CCL2-/- mice. J Cereb Blood Flow Metab 2010; 30:769-782.

[60] Lu K, Wang Y W, Wo Y Y, Yang Y L. Extracellular signal-regulated kinase-mediated IL-1-induced cortical neuron damage during traumatic brain injury. Neurosci Lett 2005; 386:40-45.

[61] Patel H C, Boutin H, Allan S M: Interleukin-1 in the brain. Mechanisms of action in acute neurodegeneration. Ann N Y Acad Sci 2003; 992:39-47.

[62] Yang G Y, Liu X H, Kadoya C, Zhao Y J, Mao Y, Davidson B L, et al. Attenuation of ischemic inflammatory response in mouse brain using an adenoviral vector to induce overexpression of interleukin-1 receptor antagonist. J Cereb Blood Flow Metab 1998; 18:840-847.

[63] Jones N C, Prior M J, Burden-Teh E, Marsden C A, Morris P G, Murphy S. Antagonism of the interleukin-1 receptor following traumatic brain injury in the mouse reduces the number of nitric oxide synthase-2-positive cells and improves anatomical and functional outcomes. Eur J Neurosci 2005; 22:72-78.

[64] Sanderson K L, Raghupathi R, Saatman K E, Martin D, Miller G, McIntosh T K. Interleukin-1 receptor antagonist attenuates regional neuronal cell death and cognitive dysfunction after experimental brain injury. J Cereb Blood Flow Metab 1999; 19:1118-1125.

[65] Hasturk A E, Yilmaz E R, Turkoglu E, Kertmen H, Horasanli B, Hayirli N, Erguder I B, Evirgen O. Therapeutic evaluation of interleukin 1-beta antagonist Anakinra against traumatic brain injury in rats. Ulus Travma Acil Cerrahi Derg 2015; 21:1-8.

[66] Relton J K, Rothwell N J. Interleukin-1 receptor antagonist inhibits ischaemic and excitotoxic neuronal damage in the rat. Brain Res Bull 1992; 29:243-246.

[67] Toulmond S, Rochwell N J. Interleukin-1 receptor antagonist inhibits neuronal damage caused by fluid percussion injury in the rat. Brain Res 1995; 671:261-266.

[68] Basu A, Krady J K, O'Malley M, Styren S D, Dekosky S T, Levison S W. The type 1 interleukin-1 receptor is essential for the efficient activation of microglia and the induction of multiple pro-inflammatory mediators in response to brain injury. J Neurosci 2002; 22:6071-6082.

[69] Tehranian R, Andell-Jonsson S, Beni S M, Yatsiv I, Shohami E, Bartfai T, Lundkvist J, Iverfeldt K. Improved recovery and delayed cytokine induction after closed head injury in mice with central overexpression of the secreted isoform of the interleukin-1 receptor antagonist. J Neurotrauma 2002; 19:939-951.

[70] Larsen C M, Faulenbach M, Vaag A, Valund A, Ehses J A, Seifiri B, Mandrup-Poulsen T, Donath M Y. Interleukin-1-receptor antagonist in type 2 diabetes mellitus. N Engl J Med 2007; 356:1517-1526.

[71] Van Tasell B W, Toldo S, Mezzaroma E, Abbate A. Contemporary reviews in cardiovascular medicine: targeting interleukin-1 in heart disease. Circulation 2013; 128:1910-1923.

[72] Lust J A, Lacy M Q, Zeldenrust S R et al. Induction of a chronic disease state in patients with smoldering or indolent multiple myeloma by targeting interleukin-1 beta induced interleukin-6 production and the myeloma proliferative component Mayo Clin Proc 2009; 84:114-122.

[73] Eichacker P Q, Parent C, Kalil A, et al. Risk and the efficacy of anti-inflammatory agents: Retrospective and confirmatory studies of sepsis. Am J Respir Crit Care Med 2002; 166:1197-1205.

[74] Emsley H C, Smith C J, Georgiou R F, et al. A randomized phase II study of interleukin-1 receptor antagonist in acute stroke patients. J Neurol Neurosurg Psychiatry 2005; 76:1366-1372.

[75] Helmy A, Guilfoyle M R, Carpenter K L H, Pickard J D, Menon D K, Hutchinson P J. Recombinant human interleukin-1 receptor antagonist in severe traumatic brain injury: a phase II randomized control trial. J Cereb Blood Flow Metab 2014; 34:845-851.

[76] Genovese M C, Cohen S, Moreland L, Lium D, Robbins S, Newmark R, Bekker P. Combination therapy with etanercept and anakinra in the treatment of patients with rheumatoid arthritis who have been treated unsuccessfully with methotrexate. Arthritis Rheum 2014; 50:1412-1419.

[77] Helson L, Green S, Carswell E, Old L J. Effect of tumor necrosis factor on cultured human melanoma cells. Nature 1975; 258:731-732.

[78] Mirza S, Hossain M, Mathews C, Martinez P, Pino P, Gay J L, Rentfro A, McCormick J B, Fisher-Hoch S P. Type-2 diabetes is associated with elevated levels of TNF-alpha, IL-6 and adiponectin and low levels of leptin in a population of Mexican Americans: a cross-sectional study. Cytokine 2012; 57:136-142.

[79] Ferrari R. The role of TNF in cardiovascular disease. Pharmacol Res 1999; 40:97-105.

[80] Nielsen O H, Ainsworth M A. Tumor necrosis factor inhibitors for inflammatory bowel disease. N Engl J Med 2013; 360:754-762.

[81] Swardfager W, Lanctot K, Rothenburg L, Wong A, Cappell J, Herrmann N. A meta-analysis of cytokines in Alzheimer's disease. Biol Psychiatry 2010; 68:930-941.

[82] Knoblach S M, Fan L, Faden A I. Early neuronal expression of tumor necrosis factor-alpha after experimental brain injury contributes to neurological impairment. J Neuroimmunol 1999; 95:115-125.

[83] Chio C C, Lin J W, Chang M W, Wang C C, Kuo J R, Yang C Z, Chang C P. Therapeutic evaluation of etanercept in a model of traumatic brain injury. J Neurochem 2010; 115:921-929.

[84] Chio C C, Chang C H, Wang C C, Cheong C U, Chao C M, Cheng B C, Yang C Z, Chang C P. Etanercept attenuates traumatic brain injury in rats by reducing early microglial expression of tumor necrosis factor-α. BMC Neurosci 2013; 14:33.

[85] Ekici M A, Uysal O, Cikriklar H I, Ozbek Z, Turgut-Cosan D, Baydemir C, Kazanci B, Hafizoglu D. Effect of etanercept and lithium chloride on preventing secondary tissue damage in rats with experimental diffuse severe brain injury. Eur Rev Med Pharmacol Sci 2014; 18:10-27.

[86] Cheong C U, Chang C P, Chao C M, Cheng B C, Yang C Z, Chio C C. Etanercept attenuates traumatic brain injury in rats by reducing brain TNF-α contents and by stimulating newly formed neurogenesis. Mediat Inflamm 2013; 620837.

[87] Wang L, Wei F X, Cen J S, Ping S N, Li Z Q, Chen N N, Cui S B, Wan Y, Liu S Y. Early administration of tumor necrosis factor-alpha antagonist promotes survival of transplanted neural stem cells and axon myelination after spinal cord injury in rats. Brain Res 2014; 1575:87-100.

[88] Chen K B, Uchida K, Nakajima H, Yayama T, Hirai T, Watanabe S, Guerrero A R, Kobayashi S, Ma W Y, Liu S Y, Baba H. Tumor necrosis factor-α antagonist reduces apoptosis of neurons and oligodendroglia in rat spinal cord injury. Spine 2011; 36:1350-1358.

[89] Shohami E, Bass R, Wallach D, Yamin A, Gallily R. Inhibition of tumor necrosis factor alpha (TNF alpha) activity in rat brain is associated with cerebroprotection after closed head injury. J Cereb Blood Flow Metab 1996; 16:378-384.

[90] Detrait E R, Danis B, Lamberty Y, Foerch P. Peripheral administration of an anti-TNF-alpha receptor fusion protein counteracts the amyloid induced elevation of hippocampal TNF-alpha levels and memory deficits in mice. Neurochem Int 2014; 72:10-13.

[91] Marchand F, Tsantoulas C, Singh D, Grist J, Clark A K, Bradbury E J, McMahon S B. Effects of etanercept and minocycline in a rat model of spinal cord injury. Eur J Pain 2009; 13:673-681.

[92] Tuttolomondo A, Pecoraro R, Pinto A. Studies of selective TNF inhibitors in the treatment of brain injury from stroke and trauma: a review of the evidence. Drug Des, Devel Ther 2014; 8:2221-2239.

[93] Tobinick E, Kim N M, Reyzin G, Rodriguez-Romanacce H, DePuy V. Selective TNF inhibition for chronic stroke and traumatic brain injury: an observational study involving 629 consecutive patients treated with perispinal etanercept. CNS Drugs 2012; 26:1051-1070.

[94] Morganti-Kossmann M C, Rancan M, Stahel P F, Kossman T. Inflammatory response in acute traumatic brain injury: a double-edged sword. Curr Opin Crit Care 2012; 8:101-105.

[95] Erta M, Quintana A, Hidalgo J. Interleukin-6, a major cytokine in the central nervous system. Int J Biol Sci 2012; 8:1254-1266.

[96] Ley E J, Clond M A, Singer M B, Shouhed D and Salim A. 116 deficiency affects function after traumatic brain injury. J Surg Res 2011; 170:253-256.

[97] Winter C D, Pringle A K, Clough G F, Church M K. Raised parenchymal interleukin-6 levels correlate with improved outcome after traumatic brain injury. Brain 2004; 127: 315-320.

[98] Conroy S M, Nguyen V, Quina L A, Blakely-Gonzales P, Ur C, Netzeband J G, Prieto A L, Gruol D L. Interleukin-6 produces neuronal loss in developing cerebellar granule neuron cultures. J Neuroimmunol 2004; 155:43-54.

[99] Kalueff A V, Lehtimaki K A, Ylinen A, Honkaniemi J, Peltola J. Intranasal administration of human IL-6 increases the severity of chemically induced seizures in rats. Neurosci Lett 2004; 365:106-110.

[100] Samland H, Huitron-Resendiz S, Masliah E, Criado J, Henriksen S J, Campbell I L. Profound increase in sensitivity to glutamatergic-but not cholinergic agonist-induced seizures in transgenic mice with astrocyte production of IL-6. J Neurosci Res 2004; 73:176-187.

[101] Yang S H, Gangidine M, Pritts T A, Goodman M D, Lentsch A B. Interleukin 6 mediates neuroinflammation and motor coordination deficits after mild traumatic brain injury and brief hypoxia in mice. Shock 2013; 40:471-475.

[102] Okada S, Nakamura M, Mikami Y, Shimazaki T, Mihara M, Ohsugi Y, Iwamoto Y, Yoshizaki K, Kishimoto T, Toyama Y, Okano H. Blockade of interleukin-6 receptor suppresses reactive astrogliosis and ameliorates functional recovery in experimental spinal cord injury. J Neurosci Res 2004; 76:265-276.

[103] Nakamura M, Okada S, Toyama Y, Okano H. Role of IL-6 in spinal cord injury in a mouse model. Clin Rev Allergy Immunol 2005; 28:197-204.

[104] Crack P J, Zhang M, Morganti-Kossmann M C, Morris A J, Wojciak J M, Fleming J K, Karve I, Wright D, Sashindranath M, Goldshmit Y, Conquest A, Daglas M, Johnston L A, Medcalf R L, Sabbadini R A, Pebay A. Anti-lysophosphatidic acid antibodies improve traumatic brain injury outcomes. J Neuroinflamm 2014; 11:37.

[105] Suzuki S, Tanaka K, Suzuki N. Ambivalent aspects of interleukin-6 in cerebral ischemia: Inflammatory versus neurotrophic aspects. J Cereb Blood Flow Metab 2009; 29:464-479.

[106] Kaneko A. Tocilizumab in rheumatoid arthritis: efficacy, safety and its place in therapy. Ther Adv Chronic Dis 2013; 4:15-21.

[107] Opal S M, DePalo V A. Anti-inflammatory cytokines. Chest 2000; 117:1162-1172.

[108] Csuka E, Morganti-Kossmann M C, Lenzlinger P M, Joller H, Trentz O, Kossmann T. IL-10 levels in cerebrospinal fluid and serum of patients with severe traumatic brain injury: Relationship to IL-6, TNF-alpha, TGF-beta1 and blood-brain barrier function. J Neuroimmunol 1999; 101:211-221.

[109] Kumar R G, Boles J A, Wagner A K. Chronic inflammation after severe traumatic brain injury: characterization and associations with outcome at 6 and 12 months post injury. J Head Trauma Rehabil 2014.

[110] Bachis A, Colangelo A M, Vicini S, Doe P P, De Bernardi M A, Brooker G, Mocchetti I. Interleukin-10 prevents glutamate-mediated cerebellar granule cell death by blocking caspase-3-like activity. J Neurosci 2001; 21:3104-3112.

[111] Knoblach S M, Faden A I. Interleukin-10 improves outcome and alters proinflammatory cytokine expression after experimental traumatic brain injury. Exp Neurol 1998; 153:143-151.

[112] Chen X, Duan X S, Xu L J, Zhao J J, She Z F, Chen W W, Zheng Z J, Jiang G D. Interleukin-10 mediates the neuroprotection of hyperaric oxygen therapy against traumatic brain injury in mice. Neuroscience 2014; 266:235-243.

[113] Bethea J R, Nagashima H, Acosta M C, Briceno C, Gomez F, Marcillo A E, Loor K, Green J, Dietrich W D. Systemically administered interleukin-10 reduces tumor necrosis factor-alpha production and significantly improves functional recovery following traumatic spinal cord injury in rats. J Neurotrauma 1999; 16:851-863.

[114] Brewer K L, Bethea J R, Yezierski R P. Neuroprotective effects of interleukin-10 following excitotoxic spinal cord injury. Exp Neurol 1999; 159:484-493.

[115] Abraham K E, McMillen D, Brewer K L. The effects of endogenous interleukin-10 on gray matter damage and the development of pain behaviors following excitotoxic spinal cord injury in the mouse. Neuroscience 2004; 124:945-952.

[116] Marlow G J, van Gent D, Ferguson L R. Why interleukin-10 supplementation does not work in Crohn's disease patients. World J Gastroenterol 2013; 19:3931-3941.

[117] Roof R L, Hoffman S W, Stein D G. Progesterone protects against lipid peroxidation following traumatic brain injury in rats. Mol Chem Neuropathol 1997; 31:1-11.

[118] Sayeed I, Stein D G. Progesterone as a neuroprotective factor in traumatic and ischemic brain injury. Prog Brain Res 2009; 175:219-237.

[119] O'Connor C A, Cernak I, Johnson F, et al. Effects of progesterone on neurologic and morphologic outcome following diffuse traumatic brain injury in rats. Exp Neurol 2007; 205:145-153.

[120] Robertson C L, Puskar A, Hoffman G E et al. Physiologic progesterone reduces mitochondrial dysfunction and hippocampal cell loss after traumatic brain injury in female rats. Exp Neurol 2006; 197:235-243.

[121] De Nicola A F, Labombarda F, Gonzalez Deniselle M C, Gonzalez S L, Garay L, Meyer M, Gargiulo G, Guennoun R, Schmacher M. Progesterone neuroprotection in traumatic CNS injury and motoneuron degeneration. Front Neuroendocrinol 2009; 30:173-187.

[122] Cutler S M, Cekic M, Miller D M, Wali B, VanLandingham J W, Stein D G. Progesterone improves acute recovery after traumatic brain injury in the aged rat. J Neurotrauma 2007; 24:1475-1486.

[123] He J, Evans C O, Hoffman S W, Oyesiku N M, Stein D G. Progesterone and allopregnanolone reduce inflammatory cytokines after traumatic brain injury. Exp Neurol 2004; 189:404-412.

[124] Chen G, Shi J, Jin W, Wang L, Xie W, Sun J, Hang C. Progesterone administration modulates TLRs/NF-kappaB signaling pathway in rat brain after cortical contusion. Ann Clin Lab Sci 2008; 38:65-74.

[125] Pan D S, Liu W G, Yang X F, Cao F. Inhibitory effect of progesterone on inflammatory factors after experimental traumatic brain injury. Biomed Environ Sci 2007; 20:432-438.

[126] Xiao G, Wei J, Yan W, Wang W, Lu Z. Improved outcomes from the administration of progesterone for patients with acute severe traumatic brain injury: a randomized controlled trial. Crit Care 2008; 12:R61.

[127] Robertson C L, Fidan E, Stanley R M, Noje C, Bayir H. Progesterone for neuroprotection in pediatric traumatic brain injury. Pediatr Crit Care Med 2015; 16:236-244.

[128] Skolnick B E, Maas A I, Narayan R K, van der Hoop R G, MacAllister T, Ward J D, Nelson N R, Stocchetti N. A clinical trial of progesterone for severe traumatic brain injury. N Engl J Med 2014; 371:2467-2476.

[129] Chase A. Traumatic brain injury. No benefit of progesterone therapy in patients with TBI. Nat Rev 2015; 11:65.

[130] Chen S F, Hung T H, Chen C C, Lin K H, Huang Y N, Tsai H C, Wang J Y. Lovastatin improves histological and functional outcomes and reduces inflammation after experimental traumatic brain injury. Life Sci 2007; 81:288-298.

[131] Li B, Mahmood A, Lu D, Wu H, Xiong Y, Qu C, Chopp M. Simvastatin attenuates microglia, astrocyte activation and decreases IL-1β level following traumatic brain injury. Neurosurgery 2009; 65:179-186.

[132] Wang H, Lynch J R, Song P, Yang H J, Yates R B, Mace B, Warner D S, Guyton J R, Laskowitz D T. Simvastatin and atorvastatin improve behavioral outcome, reduce hippocampal degeneration, and improve cerebral blood flow after experimental traumatic brain injury. Exp Neurol 2007; 206:59-69.

[133] Lai W T, Lee K T, Chu C S, Voon W C, Yen H W, Tsai L Y, Sheu S H. Influence of withdrawal of statin treatment on proinflammatory response and fibrinolytic activity in humans: an effect independent on cholesterol elevation. Int J Cardiol 2005; 98: 459-464.

[134] Lee K T, Lai W T, Chu C S, Tsai L Y, Yen H W, Voon W C, Sheu S H. Effect of withdrawal of statin on C-reactive protein. Cardiology 2004; 102:166-170.

[135] Li J J, Li Y S, Chu J M, Zhang C Y, Wang Y, Huang Y, Chen J, Yuan J Q, Huang Y L. Changes of plasma inflammatory markers after withdrawal of statin therapy in patients with hyperlipidemia. Clin Chim Acta 2006; 366:269-273.

[136] Orlando A, Bar-Or D, Salottolo K, Levy A S, Mains C W, Slone D S, Offner P J. Unintentional discontinuation of statins may increase mortality after traumatic brain injury in elderly patients: A preliminary observation. J Clin Med Res 2013; 5:168-173.

[137] Schneider E B, Efron D T, MacKenzie E J, Rivara F P, Nathens A B, Jurkovich G J. Premorbid statin use is associated with improved survival and functional outcomes in older head-injured individuals. J Trauma 2011; 71:815-819.

[138] Tapia-Perez J, Sachez-Aquilar M, Torres-Corzo J G, Gordillo-Moscoso A, Martinez-Perez P, Madeville P, de la Cruz-Mendoza E, Chalita-Williams J. Effect of rosuvas-

[138] tatin on amnesia and disorientation after traumatic brain injury (NCT003229758). J Neurotrauma 2008; 25:1011-1017.

[139] Sanchez-Aquilar M, Tapia-Perez J H, Sanchez-Rodriguez J J, Vinas-Rios J M, Martinez-Perez P, de la Cruz-Mendoza E, Sanchez-Reyna M, Torres-Corzo J G, Gordillo-Moscoso A. Effect of rosuvastatin on cytokines after traumatic brain injury. J Neurosurg 2013; 118:669-675.

[140] Rasras S, Rahbariyan F, Khezri M. The effect of simvastatin on patients with traumatic brain injury. J Inj Violence Res 2012; 4(3 Suppl 1)63.

[141] Bye N, Habgood M D, Callaway J K, Malakooti N, Potter A, Kossman T, Morganti-Kossman M C. Transient neuroprotection by minocycline following traumatic brain injury is associated with attenuated microglial activation but no changes in cell apoptosis or neutrophil infiltration. Exp Neurol 2007; 204:220-233.

[142] Ziebell J M, Morganti-Kossmann M C. Involvement of pro- and anti-inflammatory cytokines and chemokines in the pathophysiology of traumatic brain injury. Neurotherapeutics 2010; 7:22-30.

[143] Sanchez Mejia R O, Ona V O, Li M, Friedlander R M. Minocycline reduces traumatic brain injury-mediated caspase-1 activation, tissue damage, and neurological dysfunction. Neurosurgery 2001; 48:1393-1399.

[144] Lee S M, Yune T Y, Kim S J, Park D W, Lee Y K, Kim Y C, Oh Y J, Markelonis G J, Oh T H. Minocylcline reduces cell death and improves functional recovery after traumatic spinal cord injury in the rat. J Neurotrauma 2013; 20:1017-1027.

[145] Yrjanheikki J, Keinanen R, Pellikka M, Hokfelt T, Koistinaho J. Tetracyclines inhibit microglial activation and are neuroprotective in glial brain ischemia. Proc Natl Acad Sci 1998; 95:15769-15774.

[146] Uckun O M, Alagoz F, Secer M, Karakoyun O, Ocakcioglu A, Yildirim A E, Yimaz F, Sahinoglu M, Divanlioglu D, Dalgic A, Daglioglu E, Belen A D. Neuroprotective effects of tetracyclines on blunt head trauma: an experimental study on rats. J Neurosci Rural Pract 2015; 6:27-32.

[147] Kovesdi E, Kamnaksh A, Wingo D, Ahmed F, Grunberg N E, Long J B, Kasper C E, Agoston D V. Acute minocycline treatment mitigates the symptoms of mild blast-induced traumatic brain injury. Front Neurol 2012; 3:111.

[148] Stirling D P, Koochesfahani K M, Steeves J D, Tetzlaff W. Minocycline as a neuroprotective agent. Neuroscientist 2005; 11:308-322.

[149] Turtzo L, Janaria N, Lescher J, Tu J, Frank J. Efficacy of minocycline in female rats after mild diffuse traumatic brain injury (15-1B). Neurology 2015; 84: Suppl 15-1B.

[150] Tsuji M, Wilson M A, Lange M S, Johnston M V. Minocycline worsens hypoxic-ischemic brain injury in a neonatal mouse model. Exp Neurol 2004; 189:58-65.

[151] Diguet E, Gross C E, Tison F, Bezard E. Rise and fall of minocycline in neuroprotection: Need to promote publication of negative results. Exp Neurol 2004; 189:1-4.

[152] Ding K, Wang H, Xu J, Lu X, Zhang L, Zhu L. Melatonin reduced microglial activation and alleviated neuroinflammation induced neuron degeneration in experimental traumatic brain injury: Possible involvement on mTOR pathway. Neurochem Int 2014; 76:23-31.

[153] Mesenge C, Margaill I, Verrecchia C, Allix M, Boulu R G, Plotkine M. Protective effect of melatonin in a model of traumatic brain injury in mice. J Pineal Res 1998; 25:41-46.

[154] Senol N, Naziroglu M. Melatonin reduces traumatic brain injury-induced oxidative stress in the cerebral cortex and blood of rats. Neural Regen Res 2014; 9:1112-1116.

[155] Ozdemir D, Uysal N, Gonenc S, Acikgoz O, Sonmez A, Topcu A, Ozdemir N, Duman M, Semin I, Ozkan H. Effect of melatonin on brain oxidative damage induced by traumatic brain injury in immature rats. Physiol Res 2005; 54:631-637.

[156] Naseem M, Parvez S. Role of melatonin in traumatic brain injury and spinal cord injury. Scientific World J 2014; 586270:13.

[157] Zhu H T, Bian C, Yuan J C, Chu W H, Xiang X, Chen F, Wang C S, Feng H, Lin J K. Curcumin attenuates acute inflammatory injury by inhibiting the TLR4/MyD88/NF-κB signaling pathway in experimental traumatic brain injury. J Neuroinflamm 2014; 11:59.

[158] Sharma S, Ying Z, Gomez-Pinilla F. A pyrazole curcumin derivative restores membrane homeostasis disrupted after brain trauma. Exp Neurol 2010; 226:191-199.

[159] Wu A, Ying Z, Schubert D, Gomez-Pinilla F. Brain and spinal cord interaction: a dietary curcumin derivative counteracts locomotor and cognitive deficits after brain trauma. Neurorehabil Neural Repair 2011; 25:322-342.

[160] Laird M D, Sukumari-Ramesh S, Swift A E, Meiler S E, Vender J R, Dhandapani K M. Curcumin attenuates cerebral edema following traumatic brain injury in mice: a possible role for aquaporin-4? J Neurochem 2010; 113:637-648.

[161] Samini F, Samarghandian S, Borji A, Mohammadi G, Bakanian M. Curcumin pretreatment attenuates brain lesion size and improves neurological function following traumatic brain injury in rat. Pharmacol Biochem Behav 2013; 110:238-244.

[162] Cho M L, Kim W U, Min S Y, Min D J, Min J K, Lee S H, Park S H, Cho C S, Kim H Y. Cyclosporine differentially regulates interleukin-10, interleukin-15, and tumor necrosis factor α production by rheumatoid synoviocytes. Arthritis Rheum 2002; 46:42-51.

[163] Myrillas T T, Linden G J, Marley J J, Irwin C R. Cyclosporin A regulates interleukin-1beta and interleukin-6 expression in gingiva: Implications for gingival overgrowth. J Periodontol 1999; 70:294-300.

[164] Gauchat J F, Khandjian E W, Weil R. Cyclosporin A prevents induction of the interleukin 2 receptor gene in cultured murine thymocytes. Proc Natl Acad Sci 1986; 83:6430-6434.

[165] Tracey D E, Hardee M M, Richard K A, Paslay J W. Pharmacological inhibition of interleukin-1 activity on T cells by hydrocortisone, cyclosporine, prostaglandins, and cyclic nucleotides. Immunopharmacology 1988; 15:47-62.

[166] Kilbaugh T J, Bhandare S, Lorom D H, Saraswati M, Robertson C L, Margulies S S. Cyclosporin A preserves mitochondrial function after traumatic brain injury in the immature rat and piglet. J Neurotrauma 2011; 28:763-774.

[167] Hatton J, Rosbolt B, Empey P, Kryscio R, Young B. Dosing and safety of cyclosporine in patients with severe brain injury. J Neurosurg 2008; 109:699-707.

[168] Nighoghossian N, Berthezene Y, Mechtouff L, Derex L, Cho T H, Ritzenthaler T, Rheims S, Chauveau E, Bejot Y, Jacquin A, Giroud M, Ricolfi F, Philippeau F, Lamy C, Turc G, Bodiguel E, Domigo V, Guiraud V, Mas J L, Oppenheim C, Amarenco P, Cakmak S, Sevin-Allouet M, Guillon B, Desal H, Hosseini H, Sibon I, Mahagne M R, Ong E, Mewton N, Ovize M. Cyclosporine in acute ischemic stroke. Neurology 2015:84(22):2216-23.

[169] Thau-Zuchman O, Shohami E, Alexandrovich A G, Trembovler V, Leker R R. The anti-inflammatory drug carprofen improves long-term outcome and induces gliogenesis after traumatic brain injury. J Neurotrauma 2012; 29:375-384.
[170] Lee H F, Lee T S, Kou Y R. Anti-inflammatory and neuroprotective effects of triptolide on traumatic brain injury in rats. Respir Physiol Neurobiol 2012; 182:1-8.
[171] Oh J Y, Roddy G W, Choi H, Lee R H, Ylostalo J H, Rosa Jr. R H, Prockop D J. Anti-inflammatory protein TSG-6 reduces inflammatory damage to the cornea following chemical and mechanical injury. Proc Natl Acad Sci 2010; 107:16875-16880.
[172] Watanabe J, Shetty A K, Hattiangady B, Kim D K, Foraker J E, Nishida H, Prockop D J. Administration of TSG-6 improves memory after traumatic brain injury in mice. Neurobiol Dis 2013; 59:86-99.
[173] Bachstetter A D, Webster S J, Goulding D S, Morton J E, Watterson S M, Van Eldik L J. Attenuation of traumatic brain injury-induced cognitive impairment in mice by targeting increased cytokine levels with a small molecule experimental therapeutic. J Neuroinflamm 2015; 12:69-77.
[174] Zhang R, Liu Y, Yan K, Chen L, Chen X R, Li P, Chen F F, Jiang X D. Anti-inflammatory and immunomodulatory mechanisms of mesenchymal stem cell transplantation in experimental traumatic brain injury. J Neuroinflamm 2015; 10:106.
[175] Hernandez-Ontiveros D G, Tajiri N, Acosta S, Giunta B, Tan J, Borlongan C V. Microglia activation as a biomarker for traumatic brain injury. Front Neurol 2013; 4:30.
[176] Niesman I R, Schilling J M, Shapiro L A, Kellerhals S E, Bonds J A, Kleschevnikov A M, Cui W, Voong A, Krajewski S, Ali S S, Roth D M, Patel H H, Patel P M, Head B P. Traumatic brain injury enhances neuroinflammation and lesion volume in caveolin deficient mice. J Neuroinflamm 2014; 11:39.

What is claimed is:

1. A method of treating a systemic release of cytokines in a subject caused by an infectious disease comprising the steps of:
   identifying the subject in need of reduction in the widespread release of cytokines caused by the infectious disease; and
   administering one or more pharmaceutical compositions comprising a therapeutically effective amount of empty liposomes, dissolved or dispersed in a suitable aqueous or non-aqueous medium, wherein the amount of the empty liposomes or a lysophosphatidyl-monoglyceride-fatty acid eutectic is sufficient to reduce the level of cytokines in the subject, wherein the empty liposome consist essentially of a single lipid selected from a phosphatidylcholine, lysolecithin, lysophosphatidylethanol-amine, phosphatidylserine, phosphatidylinositol, phosphatidylethanolamine, cardiolipin, phosphatidic acid, cerebrosides, dicetylphosphate, dipalmitoyl-phosphatidylglycerol, stearylamine, dodecylamine, hexadecyl-amine, acetyl palmitate, glycerol ricinoleate, hexadecyl stearate, isopropyl myristate, amphoteric acrylic polymers, diacylglycerol, or diacylglycerolsuccinate.

2. The method of claim 1, wherein the one or more infectious diseases are selected from at least one of viral, bacterial, fungal, helminthic, protozoan, or hemorrhagic infectious agents.

3. The method of claim 1, wherein the one or more infectious diseases is selected from at least one of infection with an Arenaviridae, Filoviridae, Bunyaviridae, Flaviviridae, and Rhabdoviridae virus.

4. The method of claim 1, wherein the one or more infectious diseases is selected from at least one of Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses.

5. The method of claim 1, wherein the disease condition is septic shock syndrome, a chronic inflammatory response to the infectious disease, or septic shock syndrome.

6. The method of claim 1, wherein the one or more disease conditions is an adverse reaction caused by the treatment with anti-CD19 Chimeric Antigen Receptor (CAR) T cells or antitumor cell therapy, activated dendritic cells, activated macrophages, or activated B cells.

7. The method of claim 1, wherein the composition further comprises a curcumin extract, curcuminoids or synthetic curcumin are disposed in a liposome.

8. The method of claim 1, wherein the therapeutically effective amount comprises 50 nM/kg, 10 to 100 nM/kg, 25 to 75 nM/kg, 10, 20, 30, 40, 50, 60, 70, 80, 90, or 100 nM/kg of body weight of the subject.

9. The method of claim 1, wherein the composition further comprises a curcumin, or a synthetic curcumin that is 85, 86, 87, 88, 89, 90, 91, 92, 93, 94, 95 or 96% pure diferuloylmethane.

10. The method of claim 1, further comprising a curcumin or curcuminoids are selected from at least one of Artumerone, methylcurcumin, demethoxy curcumin, bisdemethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione (piperonyl curcumin) 1,7-bis(2-hydroxy naphthyl)-1,6-heptadiene-2,5-dione (2-hydroxyl naphthyl curcumin) and 1,1-bis(phenyl)-1,3,8,10 undecatetraene-5,7-dione.

11. The method of claim 1, wherein the composition consists of a lysophosphatidyl compound, a monoglyceride, and free fatty acid.

12. The method of claim 1, wherein the composition consists of a lysophosphatidyl compound, a monoglyceride, and free fatty acid and has a ratio of 1:4:2, 1:3:3, 2:4:2, or 1:2:4 mole percent.

13. The method of claim 1, wherein the composition consists of a eutectic mixture comprising a LysoPG, a myristoyl monoglyceride, and myristic acid.

14. The method of claim 1, wherein the composition comprises an active agent, and has a ratio of liposome phospholipids to an active agent of 3:1, 1:1, 0.3:1, and 0.1:1.

15. The method of claim 1, wherein the eutectic does not interact with the active agent in vivo.

16. The method of claim 1, wherein the eutectic is provided separately from the active agent to the subject.

17. The method of claim 1, wherein the eutectic is provided in an amount that reduces QT prolongation in the subject.

18. The method of claim 1, wherein the eutectic is provided in an amount that reduces an anti-inflammatory response.

19. The method of claim 1, wherein the eutectic is provided in an amount that reduces the expression or activity of at least one of IL-1β, IL-6, TNF-α, MCP-1, MIP-1, or Rantes.

* * * * *